United States Patent [19]
Hayashi et al.

[11] 3,962,312
[45] June 8, 1976

[54] 9,11,15-TRIHYDROXY PROST-5-ENOIC ACID ANALOGUES

[75] Inventors: Masaki Hayashi; Tadao Tanouchi, both of Takatsuki; Hiroyuki Ito, Suita; Isao Ohyama, Kyoto, all of Japan

[73] Assignee: Ono Pharmaceutical Company, Osaka, Japan

[22] Filed: Sept. 19, 1973

[21] Appl. No.: 398,714

[30] Foreign Application Priority Data
Sept. 21, 1972  Japan.............................. 47-94972
Mar. 23, 1973  Japan.............................. 48-33234

[52] U.S. Cl. ...................... 260/468 D; 260/209 R; 260/343.3 R; 260/345.7; 260/346.2 R; 260/473 A; 260/504; 260/514 D; 260/520 B; 260/617 R; 424/305; 424/308; 424/317

[51] Int. Cl.² .................. C07C 61/38; C07C 69/74

[58] Field of Search........ 260/514 D, 468 D, 473 A, 260/520

[56] References Cited
UNITED STATES PATENTS
3,843,713  10/1974  Finch et al........................... 260/468

FOREIGN PATENTS OR APPLICATIONS
782,822  8/1972  Belgium............................. 260/468

OTHER PUBLICATIONS
Kirton et al., Biochem. and Biophys. Research Comm. 47, 903 (1972).
Hamberg et al., J. Biol. Chem. 246, 1073, (1971).

*Primary Examiner*—Robert Gerstl
*Attorney, Agent, or Firm*—Albert H. Graddis; Frank S. Chow

[57] ABSTRACT
Prostaglandin compounds of the formula:

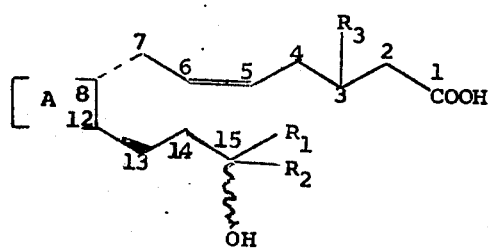

wherein A represents a grouping of formula II, III or IV indicated below and (i)$R_1$ represents an unsubstituted n-butyl, n-pentyl, n-hexyl or n-heptyl radical, or such a radical carrying one, two or three alkyl substituents of 1 to 4 carbon atoms, or $R_1$ represents a methyl, ethyl, propyl or butyl radical carrying a phenyl, cyclohexyl or cyclopentyl substituent, $R_2$ represents a hydrogen atom or an alkyl radical of 1 to 4 carbon atoms, and $R_3$ represents a hydrogen atom, or (ii) $R_1$ represents n-butyl, or n-butyl or n-pentyl carrying one, two or three alkyl substituents of 1 to 4 carbon atoms, or $R_1$ represents a methyl, ethyl, propyl or butyl radical carrying a phenyl, cyclohexyl or cyclopentyl substituent, $R_2$ represents a hydrogen atom or an alkyl radical of 1 to 4 carbon atoms, and $R_3$ represents an alkyl radical of 1 to 4 carbon atoms are disclosed. These compounds exhibit characteristic prostaglandin-like activity.

6 Claims, No Drawings

9,11,15-TRIHYDROXY PROST-5-ENOIC ACID ANALOGUES

This invention relates to a new process for the preparation of prostaglandin analogues, and to new prostaglandin analogues.

Prostaglandins are derivatives of prostanoic acid which has the following formula:

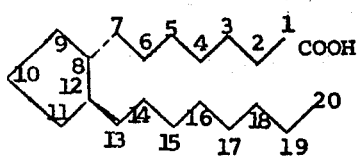

I

Various types of prostaglandins are known, the types depending on the structure and substituents on the alicyclic ring. For example, the alicyclic rings of prostaglandins E(PGE), F(PGF) and A(PGA) have the structures:

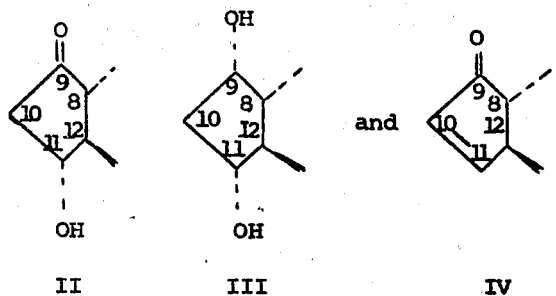

II  III  IV respectively.

Such compounds are sub-classified according to the position of double bond(s) in the side chain(s) attached to the 8- and 12-positions of the alicyclic ring. Thus PG-1 compounds have a trans-double bond between $C_{13}$–$C_{14}$, PG-2 compounds have a cis-double bond between $C_5$–$C_6$ and a trans-double bond between $C_{13}$–$C_{14}$, and PG-3 compounds have cis-double bonds between $C_5$–$C_6$ and $C_{17}$–$C_{18}$ and a trans-double bond between $C_{13}$–$C_{14}$. For example, prostaglandin $F_{1\alpha}$ ($PGF_{1\alpha}$) and prostaglandin $E_1$ ($PGE_1$) are characterized by the following structures V and VI.

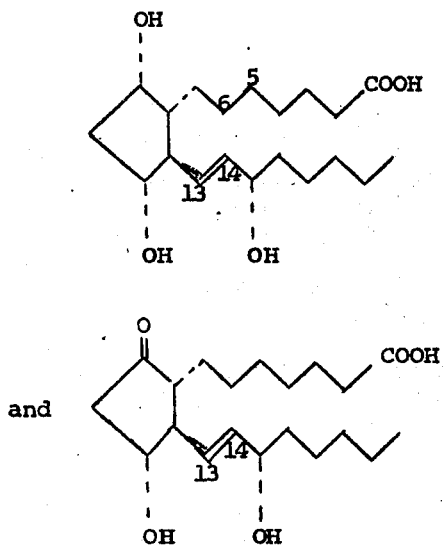

respectively. The structures of $PGF_{2\alpha}$ and $PGE_2$, as members of the PG-2 group, correspond to those of formulae V and VI respectively with a cis-double bond between the carbon atoms in positions 5 and 6. Compounds in which the double bond between the carbon atoms in positions 13 and 14 is replaced by ethylene($-CH_2CH_2-$) are known as dihydro-prostaglandins, e.g. prostaglandin-$F_{1\alpha}$ (dihydro-$PGF_{1\alpha}$) and prostaglandin-$E_1$ (dihydro-$PGE_1$).

Prostaglandins are generally known to possess pharmacological properties, for example they stimulate smooth muscle, have hypotensive and antilipolytic activities, and also inhibit blood platelet aggregation, and are, accordingly, useful in the treatment of hypertension, thrombosis, asthma and gastro-intestinal ulcers, in the induction of labour and abortion in pregnant female mammals, and in the prevention of arteriosclerosis. They are fat-soluble substances obtainable in very small quantities from various tissues of animals which secrete the prostaglandins in the living body.

The present invention is concerned with dihydro-prostaglandins which possess the pharmacological properties of the fundamental prostaglandins and have the advantage thereover in at least being able to withstand the enzymatic transformation of prostaglandin-15-hydroxy-dehydrogenase which causes deactivation of prostaglandins.

Certain dihydro-prostaglandins have hitherto been described. For example, in Canadian Pat. No. 887628 (granted to B. Samuelsson) a process is described and claimed for the preparation of 13,14-dihydro-$PGE_2$ compounds which involves the reduction of the $C_{13}$–$C_{14}$ double bond of $PGE_2$ compounds by means of enzymes present in a variety of animal tissues, for example a reductase enzyme of mammalian lung, kidney or intestine tissue. The use of such enzymes for the preparation of dihydroprostaglandins is expensive and inconvenient.

It has now been found as a result of research and experimentation that 13,14-dihydro-prostaglandins can be prepared by a process which does not necessitate the use of a reductase enzyme.

The present invention is concerned with a new process for the preparation of 13,14-dihydro-prostaglandins of the general formula:

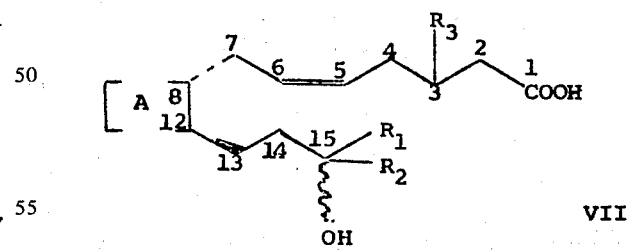

VII wherein A represents a grouping of formula II, III or IV indicated above and (i)$R_1$ represents an unsubstituted n-butyl, n-pentyl, n-hexyl or n-heptyl radical, or such a radical carrying one, two or three alkyl substituents of 1 to 4 carbon atoms, or $R_1$ represents a methyl, ethyl, propyl or butyl radical carrying a phenyl, cyclohexyl or cyclopentyl substituent, $R_2$ represents a hydrogen atom or an alkyl radical of 1 to 4 carbon atoms, and $R_3$ represents a hydrogen atom, or (ii) $R_1$ represents n-butyl, or n-butyl or n-pentyl carrying one, two or three alkyl substituents of 1 to 4 carbon atoms, or $R_1$ represents a methyl, ethyl, propyl or butyl radical carrying a phenyl, cyclohexyl or cyclopentyl substituent, $R_2$ represents a hydrogen atom or an alkyl radical of 1 to 4 carbon atoms, and $R_3$ represents an alkyl radical of 1 to 4 carbon atoms.

The present invention is concerned with all compounds of general formula VII in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VII have at least three centres of chirality, these three centres of chirality being at the alicyclic ring carbon atoms in the positions of group A identified as 8 and 12 and at the C-15 carbon atom which has attached to it an α-hydroxy radical and a β-hydroxy radical and the mixture of them.

Still further centres of chirality occur when the alicyclic group A carries a hydroxy radical on the carbon atom in position 11 (i.e. when the ring is that of formula II) or hydroxy radicals in positions 9 and 11 (i.e. when the ring is that of formula III), and when $R_3$ represents an alkyl radical. The presence of chirality leads, as is well known, to the existence of isomerism. However, the compounds of general formula VII all have such a configuration that the side chains attached to the ring carbon atoms in the positions identified as 8 and 12 are trans with respect to each other. Accordingly, all isomers of general formula VII, and mixtures thereof, which have those side-chains attached to the ring carbon atoms in positions 8 and 12 in the trans configuration and have an α-hydroxy radical and β-hydroxy radical and the mixture of them in the 15-position are to be considered within the scope of general formula VII. The hydroxy radical(s) in the alicyclic ring, when present, also has the α-configuration.

According to the present invention the 13,14-dihydro-prostaglandin compounds of general formula VII are prepared by the process which comprises reacting a bicyclo-octane derivative of the general formula:

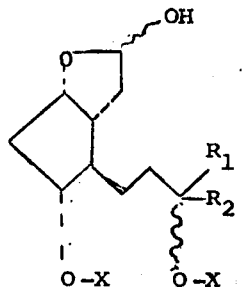

VIII (wherein X represents a 2-tetrahydropyranyl group unsubstituted or substituted by at least one alkyl group, or a tetrahydrofuranyl or 1-ethoxyethyl group, and is preferably 2-tetrahydropyranyl, and $R_1$ and $R_2$ are as hereinbefore defined) with a phosphorane compound of the general formula:

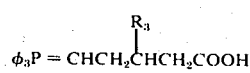

IX (wherein ϕ represents the phenyl radical and $R_3$ is as hereinbefore defined) to obtain a compound of the general formula:

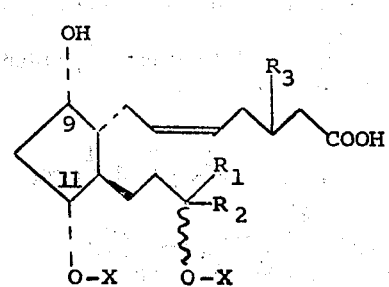

X (wherein $R_1$, $R_2$, $R_3$ and X are as hereinbefore defined), optionally converting by methods known per se the 9α-hydroxy radical to an oxygen atom, and converting the —OXO groups in the resulting compound by methods known per se to hydroxy radicals to obtain a 13,14-dihydro-prostaglandin of the general formula:

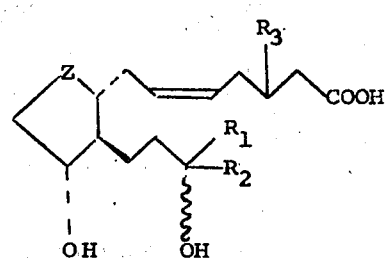

XI (wherein Z represents

or C=O, and $R_1$, $R_2$ and $R_3$ are as hereinbefore defined) and, if desired, converting by methods known per se the PGE alicyclic ring (Z represents C=O) into that of a PGA (formula IV) compound. By the term "methods known per se" as used in this Specification is meant methods heretofore used or described in the chemical literature.

The intermediate compounds of general formula X, which are new compounds and as such constitute a feature of the invention, may thus be converted into 13,14-dihydro-prostaglandins of general formula VII by the reactions depicted schematically below

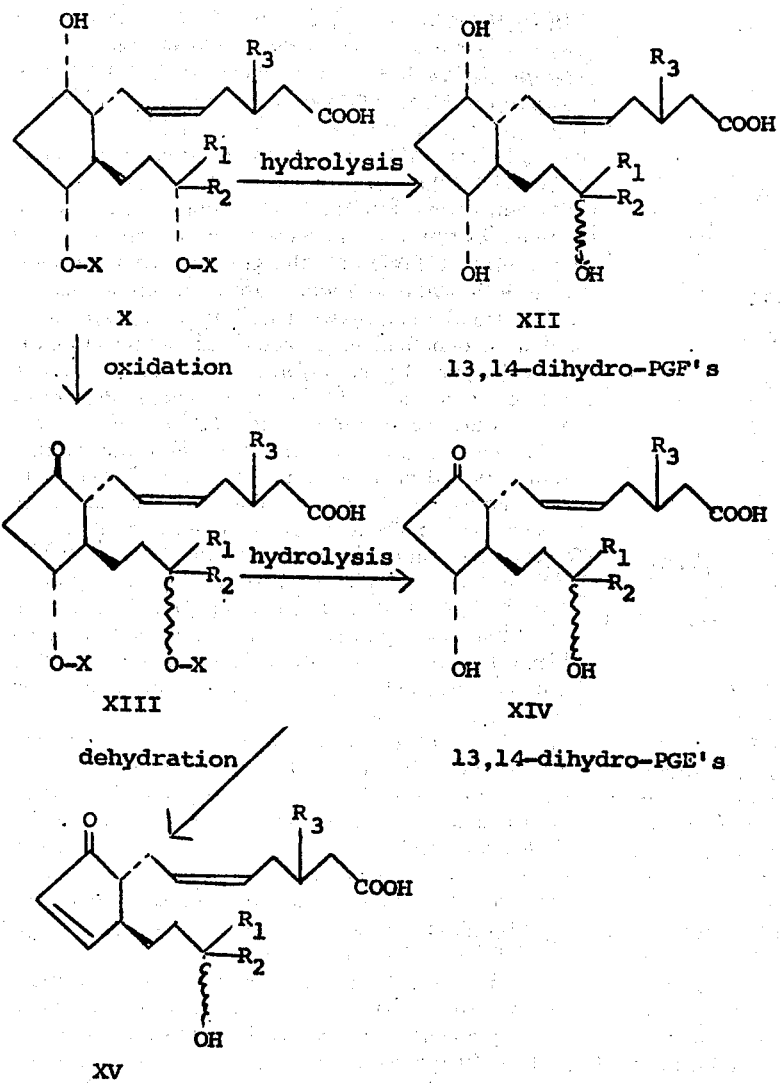

13,14-dihydro-PGA's

The groups —OX (wherein X is as hereinbefore defined) in the intermediate compounds of formula X may be converted into hydroxy radicals by mild hydrolysis with an aqueous solution of an organic acid, e.g. acetic acid, or with a dilute inorganic acid, for example, by heating the compounds of formula X at 30°–60°C. (preferably at a temperature below 45°C) with an acid mixture, such as a mixture of acetic acid, water and tetrahydrofuran, or a mixture of hydrochloric acid with tetrahydrofuran or methanol. Such a procedure is particularly suitable when symbol X in the compounds of general formula X represents a 2-tetrahydropyranyl group.

The PGF alicyclic ring in the compounds of general formula X can be converted into a PGE ring (cf. formula XIII) by methods known per se for the conversion of a hydroxy group in the 9-position of a prostaglandin to an oxo radical, for example by means of a chromic acid solution (e.g. obtained from chromium trioxide, manganese sulphate and water).

The dihydro-PGE compounds of general formula XI (Z represents C=O) and XIV can be converted into corresponding PGA compounds by methods known per se, for example by subjecting the PGE's to dehydration using an aqueous solution of an organic or inorganic acid having a higher concentration than that employed for hydrolysis of compounds insluble formula X to those of formula XI, e.g. 1N hydrochloric acid.

The reaction between the bicyclo[3,3,0]octanes of formula VIII with the phosphorane compounds of formula IX is carried out under the normal conditions utilized for effecting the Wittig reaction, e.g. in an inert solvent at ambient temperature. The reaction is preferably carried out in dimethylsulphoxide because the compounds of formula IX are practically insoluble in other solvents, e.g. tetrahydrofuran, and because a cis-double bond must be formed stereospecifically in the Wittig reaction. For the better performance of the Wittig reaction more than two molecular equivalents of the phosphorane compound are required for each mole of the bicyclo-octane reactant. Reaction between the compounds of formulae VIII and IX is generally effected at a temperature of 10°–40°C, preferably at 20°–30°C, and is usually complete after about 30 minutes to four hours at laboratory temperature. The acid product of formula X may be extracted from the reaction mixture by conventional procedures and further purified by column chromatography on silica gel.

The bicyclo-octane starting materials of general formula VIII can be prepared by the series of reactions depicted schematically below:

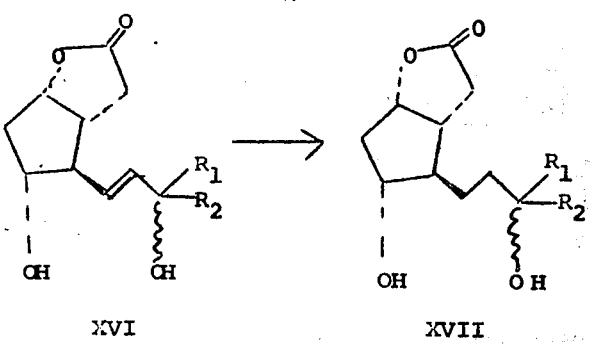

XVI            XVII

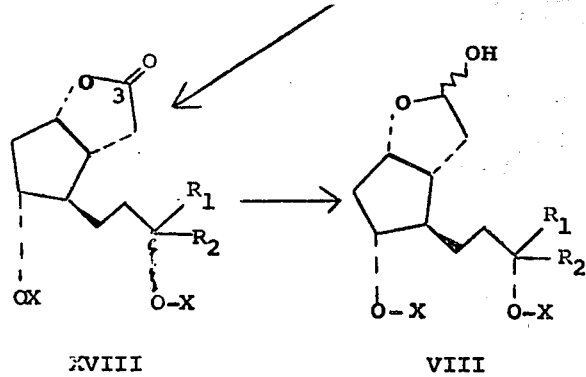

XVIII           VIII wherein $R_1$ and $R_2$ are as hereinbefore defined.

The compounds of formula XVI are dissolved in a suitable solvent, e.g. methanol or ethanol, and then subjected to catalytic hydrogenation in the presence of a catalyst effective for the reduction of the double bond to ethylene ($-CH_2CH_2-$), for example palladium on charcoal, palladium black or platinum dioxide. The resulting compounds of formula XVII are then reacted with a dihydropyran, dihydrofuran or ethyl vinyl ether in an inert organic solvent, such as methylene chloride, in the presence of a condensing agent, for example p-toluene-sulphonic acid, to obtain the compounds of formula XVIII. Those compounds are then reduced at a low temperature, preferably below $-50°C$., with a reagent capable of reducing the oxo radical in the position indicated as 3 to a hydroxy radical, preferably using diisobutylaluminium hydride.

The compounds of general formula XVI can be prepared using initially 2-oxa-3-oxo-6-syn-formyl-7-antiacetoxy-cis-bicyclo[3,3,0]octane (E.J. Corey et al, J. Amer. Chem. Soc. 91, p.5675) and applying thereto known procedures [see, for example, J. Amer. Chem. Soc. 92, 397 (1970).

The phosphorane starting materials of general formula IX can be prepared by reacting sodiomethylsulphinylcarbanide with a 4-carboxy-butyl-triphenylphosphonium halide of the formula:

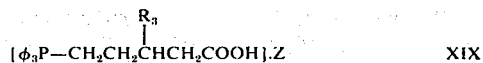

XIX (wherein Z represents a halogen, preferably bromine, atom, and $\phi$ and $R_3$ are as hereinbefore defined) in an organic solvent such as dimethylsulphoxide.

The compounds of formula XIX can be obtained by converting 5-hydroxy-pentanoic acid, optionally carrying on the 3-position an alkyl substituent of 1 to 4 carbon atoms, by methods known per se into a 5-halo(-preferably bromo)-pentanoic acid and heating the halo compound with triphenylphosphine in an inert solvent.

The 13,14-dihydro-prostaglandins of general formula VII obtained by the process of the present invention can be converted into salts or esters, preferably alkyl esters containing 1 to 12 carbon atoms.

The salts may be prepared from the compounds of general formula VII by methods known per se, for example by reaction of stoichiometric quantities of compounds of general formula VII and the appropriate base, e.g. an alkali metal hydroxide or carbonate, ammonium hydroxide, ammonia or an amine, in a suitable solvent. The salts may be isolated by lyophilisation of the solution or, if sufficiently insoluble in the reaction medium, by filtration, if necessary after removal of part of the solvent. Preferably the salts are non-toxic salts, i.e. salts the cations of which are relatively innocuous to the animal organism when used in therapeutic doses so that the beneficial pharmacological properties of the prostaglandins of general formula VII are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The esters of 13,14-dihydro-prostaglandins of general formula VII can be obtained by reaction of the acids with (i) diazoalkane compounds, e.g. diazomethane, (ii) alcohols or thiols in the presence of dicyclohexylcarbodiimide as condensing agent, or (iii) alcohols following the formation of a mixed acid anhydride by adding a tertiary amine and then a pivaloyl halide or an arylsulphonyl or alkylsulphonyl halide (cf. our Belgian Pat. Nos. 775106 and 776294).

The 13,14-dihydro-prostaglandins of general formula VII can also be converted into prostaglandin alcohols, i.e. compounds in which the carboxy radical is replaced by the hydroxymethylene (i.e. $-CH_2OH$) group, of the general formula:

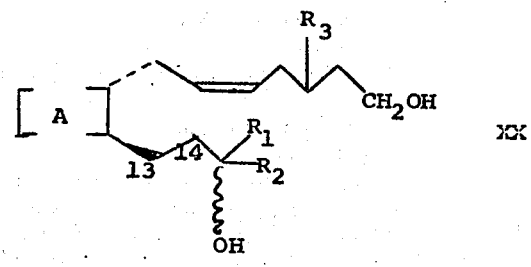

XX wherein A, $R_1$, $R_2$ and $R_3$ are as hereinbefore defined.

The 13,14-dihydro-prostaglandin alcohols of general formula XX can be prepared from the acids of general formula VII by application of the method described by Pike, Lincoln and Schneider in J. Org. Chem. 34, 3552–3557 (1969), for example by converting the acids of general formula VII into their methyl esters and then the esters into oximes, and reducing the oximes with lithium aluminium hydride to form oxime alcohols, and hydrolyzing them with, for example, acetic acid. The alcohol derivatives of prostaglandins of general formula XX possess pharmacological properties similar to the acids of general formula VII from which they are derived.

The prostaglandin compounds of general formula VII and esters thereof, and corresponding alcohols of general formula XX may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70°C. during the preparation of the cyclodextrin clathrates. $\alpha$, $\beta$ or $\gamma$-Cyclodextrins or mixtures thereof may be used in the preparation of the cyclodextrin clathrates. Conversion into their cyclodextrin clathrates serves to increase the stability of the prostaglandin compounds.

Prostaglandin compounds obtained by the process of the present invention and esters and alcohol derivatives thereof, and their cyclodextrin clathrates, and non-toxic salts, possess the valuable pharmacological properties typical of prostaglandins in a selective fashion including, in particular, hypotensive-activity, inhibitory activity on gastric acid secretion and gastric ulceration, bronchodilator activity, luteolytic activity, stimulatory activity on uterine contraction and stimulatory activity on intestinal contraction, and are useful in the treatment of hypertension, in the treatment of gastric ulceration, in the treatment of asthma, in the control of oestrus in female mammals, in the prevention of pregnancy in female mammals and in the induction of labour in pregnant female mammals. In particular, 13,14-dihydro-PGA$_2$, 16(R)-methyl-13,14-dihydro-PGA$_2$, 15($\xi$)-methyl-13,14-dihydro-PGA$_2$, 15($\xi$),16(R)-dimethyl-13,14-dihydro-PGA$_2$, 16,16-dimethyl-13,14-dihydro-PGA$_2$, 16($\xi$)-phenyl-$\omega$-trinor-13,14-dihydro-PGA$_2$, 16($\xi$)-cyclohexyl-$\omega$-trinor-13,14-dihydro-PGA$_2$, 16($\xi$)-cyclopentyl-$\omega$-trinor-13,14-dihydro-PGA$_2$, 15($\xi$)-methyl-13,14-dihydro-PGE$_2$, 16($\xi$)-cyclopentyl-$\omega$-trinor-13,14-dihydro-PGE$_2$ and, more particularly, 13,14-dihydro-PGE$_2$, 15($\xi$),16(R)-dimethyl-13,14-dihydro-PGE$_2$, 16($\xi$)-phenyl-$\omega$-trinor-13,14-dihydro-PGE$_2$, 16($\xi$)-cyclohexyl-$\omega$-trinor-13,14-dihydro-PGE$_2$, 16(R)-methyl-13,14-dihydro-PGE$_2$ methyl ester, 16(R)-methyl-13,14-dihydro-PGE$_2$ isobutyl ester, 16(R)-methyl-13,14-dihydro-PGE$_2$ decyl ester and, more especially, 16(R)-methyl-13,14-dihydro-PGE$_2$ are of value in the treatment of hypertension; 15($\xi$),16(R)-dimethyl-13,14-dihydro-PGE$_2$, 16,16-dimethyl-13,14-dihydro-PGE$_2$ and, particularly, 13,14-dihydro-PGE$_2$, 15($\xi$)-methyl-13,14-dihydro-PGE$_2$, 16($\xi$)-phenyl-$\omega$-trinor-13,14-dihydro-PGE$_2$, 16($\xi$)-cyclohexyl-$\omega$-trinor-13,14-dihydro-PGE$_2$, 16($\xi$)-cyclopentyl-$\omega$-trinor-13,14-dihydro-PGE$_2$, 16(R)-methyl-13,14-dihydro-PGE$_2$ decyl ester and, more especially, 16(R)-methyl-13,14-dihydro-PGE$_2$, 16(R)-methyl-13,14-dihydro-PGE$_2$ methyl ester and 16(R)-methyl-13,14-dihydro-PGE$_2$ isobutyl ester are of value in the treatment of gastric ulceration; 13,14-dihydro-PGE$_2$, 15($\xi$)-methyl-13,14-dihydro-PGE$_2$, 16,16-dimethyl-13,14-dihydro-PGE$_2$, 15($\xi$),16(R)-dimethyl-13,14-dihydro-PGE$_2$, 16($\xi$)-phenyl-$\omega$-trinor-13,14-dihydro-PGE$_2$, 16($\xi$)-cyclohexyl-$\omega$-trinor-13,14-dihydro-PGE$_2$ and, more particularly, 16(R)-methyl-13,14-dihydro-PGE$_2$ and 16(R)-methyl-13,14-dihydro-PGE$_2$ decyl ester are of value in the treatment of asthma; (16(R)-methyl-13,14-dihydro-PGE$_2$ and its decyl ester each have a less irritant effect on the throat than PGE$_1$ when aerosols containing these prostaglandin compounds are inhaled); 13,14-dihydro-PGE$_2$, 16(R)-methyl-13,14-dihydro-PGF$_{2\alpha}$, 16($\xi$)-cyclohexyl-$\omega$-trinor-13,14-dihydro-PGF$_{2\alpha}$, 16($\xi$)-phenyl-$\omega$-trinor-13,14-dihydro-PGF$_{2\alpha}$, 15($\xi$),16 (R)-dimethyl-13,14-dihydro-PGF$_{2\alpha}$, 16($\xi$)-cyclopentyl-$\omega$-trinor-13,14-dihydro-PGF$_{2\alpha}$ and 15($\xi$)-methyl-13,14-dihydro-PGF$_{2\alpha}$ are of value in the control of oestrus and the prevention of pregnancy in female mammals, 13,14-dihydro-PGF$_2$, 16(R)-methyl-13,14-dihydro-PGF$_{2\alpha}$, 15($\xi$)-methyl-13,14-dihydro-PGF$_{2\alpha}$ and 15($\xi$),16(R)-dimethyl-13,14-dihydro-PGF$_{2\alpha}$ are of value in the induction of labour in pregnant female mammals. The prostaglandin compounds of the present invention and, in particular, 15($\xi$),16(R)-dimethyl-13,14-dihydro-PGE$_2$, 16,16-dimethyl-13,14-dihydro-PGE$_2$, 15($\xi$)-methyl-13,14-dihydro-PGE$_2$, 16($\xi$)-phenyl-$\omega$-trinor-13,14-dihydro-PGE$_2$, 16($\xi$)-cyclohexyl-$\omega$-trinor-13,14-dihydro-PGE$_2$, 16($\xi$)-cyclopentyl-$\omega$-trinor-13,14-dihydro-PGE$_2$ and 16(R)-methyl-13,14-dihydro-PGE$_2$ have relatively low potencies in inducing diarrhoea in comparison with their potencies in respect of the valuable properties hereinbefore described and may accordingly be used for these purposes at appropriate rates of administration which do not induce diarrhoea as an undesired side effect.

Esters of 13,14-dihydro-prostaglandins of general formula VII are, in general, more stable to heating than the corresponding free acid. For example, the methyl, isobutyl and decyl esters of 16(R)-methyl-13,14-dihydro-PGE$_2$ each have a similar stability to heating and are each more stable to heating than 16(R)-methyl-13,14-dihydro-PGE$_2$. Thus, when each of the aforementioned prostaglandin compounds is heated at 100° ± 5°C. in a sealed container, the percentage decomposition of the esters is 0%, 2–3%, 5% and 7–8% after half an hour, 1 hour, 2 hours and 4 hours respectively, while the corresponding percentage decompositions of the free acid 16(R)-methyl-13,14-dihydro-PGE$_2$ are 50%, 75%, 90% and 100% respectively.

All the 13,14-dihydro-prostaglandins of general formula VII, with the exclusion of those compounds wherein A represents the PGE radical of formula II, R$_1$ represents the n-pentyl radical, and R$_2$ and R$_3$ represent hydrogen atoms (i.e. dihydro-PGE$_2$) are new compounds, and as such they, and their esters and alcohol derivatives conforming to general formula XX, and cyclodextrin clathrates of such acids, esters and alcohol derivatives, and non-toxic salts of such acids, constitute a very important aspect of the invention.

The following Examples and Reference Examples illustrate the process of the present invention and products thereof. It is to be understood that reference in the Examples to tetrahydropyranyl means the 2-tetrahydropyranyl group.

REFERENCE EXAMPLE 1

Preparation of
2-oxa-3-oxo-6-syn-(3$\alpha$-hydroxyoctyl)-7-anti-hydroxy-cis-bicyclo[3,3,0]octane 15 g. of 5% palladium on charcoal were suspended in 300 ml. of ethanol and the suspension placed in an apparatus suitable for a catalytic reduction. After replacing the air in the container with hydrogen, a solution of 30 g. of 2-oxa-3-oxo-6-syn-(3$\alpha$-hydroxyoct-trans-1-enyl)-7-anti-hydroxy-cis-bicyclo[3,3,0]octane in 150 ml. of ethanol was added. The compound was subjected to catalytic reduction at 20°C. for about 2 hours. After completion of the reaction, the catalyst was separated by filtration and the filtrate concentrated under reduced pressure. The residue was subjected to column chromatography with 600 g. of silica gel using benzene-ethanol (100:5 – 100:10) as eluent to obtain 15 g. of the pure title compound as a colourless oil; yield 50%. infra-red (hereinafter abbreviated to IR) absorption spectrum (liquid film): 3400, 2970 – 2860, 1775, 1460, 1420, 1375, 1315, 1200, 1090, 1055, 900 cm$^{-1}$; nuclear magnetic resonance (hereinafter abbreviated to NMR) spectrum (chloroform deuteride — hereinafter abbreviated to CDCl$_3$ — solution): δ= 5.32 – 4.92 (1H,

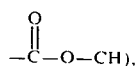

4.32 – 3.75 (2H, HO—CH), 3.63 (2H, OH); thin-layer (hereinafter abbreviated to TL) chromatography (ethyl acetate – acetic acid – isooctane – water; 90:20:50:100): Rf = 0.31.

REFERENCE EXAMPLE 2

Preparation of
2-oxa-3-oxo-6-syn-(3α-tetrahydropyranyloxy-octyl)-7-anti-tetrahydropyranyloxy-cis-bicyclo[3,3,0]octane 15.0 g. of 2-oxa-3-oxo-6-syn-(3α-hydroxyoctyl)-7-anti-hydroxy-cis-bicyclo[3,3,0]octane [prepared as described in Reference Example 1] were dissolved in 150 ml. of methylene chloride, and the mixture was reacted with 15 ml. of dihydropyran and 100 mg. of p-toluenesulphonic acid at 25°C. for 15 minutes to obtain 24.3 g. of the title compound as a pale yellow oil; yield 100%. IR absorption spectrum (liquid film): 2950, 2860, 1780, 1470 – 1440 (three pieces), 1380, 1240, 1180 – 1130 (several pieces), 1080, 1030 cm$^{-1}$; TL chromatography (methylene chloride – methanol; 20:1): Rf = 0.90.

REFERENCE EXAMPLE 3

Preparation of
2-oxa-3α-hydroxy-6-syn-(3α-tetrahydro-pyranyloxy-octyl)-7-anti-tetrahydropyranyloxy-cis-bicyclo[3,3,-0]octane 24.3 g. of 2-oxa-3-oxo-6-syn-(3α-tetrahydropyranyloxy-octyl)-7-anti-tetrahydropyranyloxy-cis-bicyclo-[3,3,0]octane [prepared as described in Reference Example 2] were reduced at 60°C. for 20 minutes with 19.8 g. of diisobutylaluminium hydride in toluene to obtain 24.4 g. of the title compound as a colourless oil; yield 100%. IR absorption spectrum (liquid film): 3400, 2950, 2860, 1450, 1360, 1200, 1130, 1080, 1020 cm$^{-1}$; TL chromatography (methylene chloride – methanol; 20:1): Rf = 0.43;

Elementary analysis: Calcd. for C$_{25}$H$_{44}$O$_6$ : C, 68.18%. H, 10.00%; Found: C,68.24%, H, 10.12%.

EXAMPLE 1

Preparation of
9α-hydroxy-11α,15α-ditetrahydropyranyloxy-prost-cis-5-enoic acid 11.9 g. of sodium hydroxide (52% content) was added to 135 ml. of dimethylsulphoxide, and the mixture was heated and stirred at 65°–70°C. for about 1 hour until forming ceased to obtain sodiomethylsulphinylcarbanide. The reaction mixture was allowed to cool to room temperature and then added dropwise to a solution of 61.5 g. of 4-carboxy-n-butyl-triphenyl-phosphonium bromide in 120 ml. of dimethylsulphoxide, the reaction temperature being kept within the range of 20°–25°C. The solution became a bright reddish colour about half way through the addition.

A solution of 24.5 g. of 2-oxa-3-hydroxy-6-syn-(3α-tetrahydropyranyloxy-octyl)-7-anti-tetrahydropyranyloxy-cis-bicyclo[3,3,0]octane [prepared as described in Reference Example 3] in 50 ml. of dimethylsulphoxide was added, and the mixture stirred vigorously at room temperature for about 2 hours. The reaction mixture was poured into 1 liter of ice-water and neutral substance extracted with a mixture of ethyl acetate and diethyl ether (1:1). The aqueous layer was acidified to pH 2.0 with a saturated aqueous solution of oxalic acid and extracted with a mixture of diethyl ether and n-pentane (1:1). The extract, after washing with water, was dried with sodium sulphate and concentrated under reduced pressure. The residue was subjected to column chromatograhy with 200 g. of silica gel using benzene-ethanol (100:5) as eluent to obtain 14.0 g. of pure 9α-hydroxy-11α,15α-ditetrahydropyranyloxy-prost-cis-5-enoic acid as a colourless oil; yield 48%. IR absorption spectrum (liquid film): 3450, 2920, 2850, – 2400, 1710, 1450 – 1440, 1400, 1380, 1350, 1320, 1250, 1200, 1130 – 1110, 1080, 1020, 730 cm$^{-1}$; NMR spectrum (CDCl$_3$ solution): δ = 5.70 – 5.18 (2H, cis CH=CH), 4.73 –4.45 (2H, 0—CH—0), 4.17 (2H, OH), 4.25 – 3.40 (7H, 0—CH, 0—CH$_2$); TL chromatography (methylene chloride: methanol): Rf = 0.38;

Elemental analysis: Calcd. for C$_{30}$H$_{52}$O$_7$: C, 68.20% H, 9.92%. Found: C, 68.34%; H, 9.86%.

EXAMPLE 2

Preparation of 13,14-dihydro-PGF$_{2α}$ 2.1 g. of 9α-hydroxy-11α,15α-ditetrahydropyranyloxy-prost-cis-5-enoic acid [prepared as described in Example 1] was dissolved in 60 ml. of a mixture of acetic acid, water and tetrahydrofuran (20:10:3), and the reaction mixture was stirred vigorously at 40° – 45°C. for 1.5 hours. The reaction mixture was then poured into 250 ml. of ice-water and extracted with ethyl acetate. The obtained ethyl acetate layer was washed with water, dried with sodium sulphate and concentrated under reduced pressure. The residue was then subjected to column chromatography with 80 g. of silica gel using cyclohexane-ethyl acetate (1:3) as eluent to obtain 90.2 g. of pure 13,14-dihydro-PGF$_{2α}$ in the form of a colourless oil; yield 63%. IR absorption spectrum (liquid film); 3370, 3010 – 2860, 2300, 1710, 1450, 1405, 1380, 1245, 1110, 1050 cm$^{-1}$; NMR spectrum (CDCl$_3$ solution): δ = – 5.33 (2H, =CH), 4.47 (4H, OH), 4.26 – 3.80 (2H, C$_9$, C$_{11}$ proton), 3.80 – 3.50 (1H, C$_{15}$ proton); TL chromatography (ethyl acetate – formic acid; 400:1): Rf = 0.27.

EXAMPLE 3

A. Preparation of 13,14-dihydro-PGE$_2$ 7.5 g. of 9α-hydroxy-11α,15α-ditetrahydropyranyloxy-prost-cis-5enoic acid [prepared as described in Example 1] were dissolved in 250 ml. of diethyl ether. The solution was cooled to 0°– 5°C., and then 250 ml. of a chromic acid solution (prepared by dissolving 3.2 g. of chromium trioxide, 10.8 g. of manganese sulphate and 3.56 ml. of sulphuric acid in water to make the total volume 80 ml.) was added and the reaction mixture stirred vigorously at 0°–5°C. for 2 hours. The reaction mixture was then saturated with sodium sulphate and extracted with diethyl ether and ethyl acetate. The extracts were combined, washed sufficiently with water, dried with sodium sulphate and then concentrated under reduced pressure. The residue was dissolved in 150 ml. of a mixture of acetic acid, water and tetrahydrofuran (65:35:10) and stirred for 3.5 hours at 38+C. The reaction mixture was then poured into 500 ml. of ice-water, extracted with ethyl acetate, washed with water, dried with sodium sulphate and then concentrated under reduced pressure. The residue was purified by column chromatography with 130 g. of silica gel using cyclohexane – ethyl acetate (1:1) as eluent to obtain the title compound as a colourless oil; yield 2.75 g. (54%). IR absorption spectrum (liquid film): 3400, 3015 – 2860, 2300, 1740, 1710, 1455, 1410, 1380, 1250, 1165, 1080, 1055 cm$^{-1}$; NMR spectrum (CDCl$_3$ solution): $\delta = 5.50 - 5.34$ (2H, =CH), 4.40 – 3.86 (4H, OH, C$_{11}$ proton), 3.82 – 3.50 (1H, C$_{15}$ proton), 2.73 (1H, C$_{10}\beta$ proton); TL chromatography (ethyl acetate - formic acid; 400:1): Rf = 0.48.

B. Preparation of 13,14-dihydro-PGA$_2$ 300 mg. of 13,14-dihydro-PGE$_2$ [prepared as described in (A) above] were dissolved in 50 ml. of a mixture of tetrahydrofuran and 1N hydrochloric acid (1:1) and the solution was stirred for 3 hours at 60°C. The reaction mixture was then diluted with ethyl acetate, washed with water, dried with magnesium sulphate and concentrated under reduced pressure. The residue was purified by column chromatography with 15 g. of silica gel using cyclohexane-ethyl acetate (8:2) as eluent to obtain 13,14-dihydro-PGA$_2$ as a colourless oil; yield 172 mg. (60%). IR absorption spectrum (liquid film): 3400, 3010 – 2850, 2340, 1740, 1710, 1585, 1450, 1400, 1380, 1360, 1245, 1050 cm$^{-1}$; NMR spectrum (CDCl$_3$ solution): $\delta = 7.60$ (1H, C$_{11}$ proton), 6.14 (1H, C$_{10}$ proton), 5.55 – 5.32 (2H, =C—H), 4.81 (2H, OH), 3.80 — 3.52 (1H, 0-CH); TL chromatography (ethyl acetate – formic acid; 400:1): Rf = 0.67.

REFERENCE EXAMPLE 4

Preparation of
2-oxa-3-oxo-6-syn-(3α-hydroxydecyl)-7-anti-hydroxy-cis-bicyclo[3,3,0]octane 23.1 G. of 2-oxa-3-oxo-6-syn-(3α-hydroxydec-1-enyl)-7-anti-hydroxy-cis-bicyclo[3,3,0]octane were dissolved in 230 ml. of ethanol and subjected to catalytic reduction in the presence of 2.5 g. of 5% palladium on charcoal at normal temperature and pressure for about 2 hours until the calculated amount of hydrogen was used up. The catalyst was removed by filtration, and the filtrate concentrated under reduced pressure. The residue was subjected to column chromatography with 400 g. of silica gel using benzene-ethanol (20:1) as eluent to obtain 15.0 g. (64.5%) of the desired product as a colourless oil. IR absorption spectrum (liquid film): 3400, 2950, 2860, 1765, 1465, 1370, 1240, 1185, 1045 cm$^{-1}$; NMR spectrum (in CDCl$_3$, TMS as internal standard): δ: 0.90 (3H, multiplet), 1.05 –3.0 (22H, multiplet), 2.9 – 3.2 (2H, —OH), 3.40 – 3.8 (1H, multiplet), 3.8 – 4.25 (1H, multiplet), 4.78 – 5.23 (1H, multiplet)$_{ppm}$.

REFERENCE EXAMPLE 5

Preparation of
2-oxa-3-oxo-6-syn-3α-hydroxyheptyl)-7-anti-hydroxy-cis-bicyclo[3,3,0]octane 19.6 g. of 2-oxa-3-oxo-6-syn-(3α-hydroxyhept-1-enyl)-7-antihydroxy-cis-bicyclo[3,3,0]octane dissolved in 200 ml. of ethanol was subjected to catalytic reduction in the presence of 5% palladium on charcoal using the same method described in Reference Example 4. Column chromatography of the crude product gave 12.1 g. (61.3%) of the desired product as a colorless oil. IR absorption spectrum (liquid film): 3400, 2930, 2860, 1760, 1460, 1375, 1240, 1185, 1045 cm$^{-1}$; NMR spectrum (in CDCl$_3$, TMS as internal standard): δ: 0.89 (3H, triplet), 1.05 – 2.95 (16H, multiplet), 3.4 – 3.8 (3H, multiplet, OH), 3.8 – 4.25 (1H, multiplet), 4.80 – 5.25 (1H, multiplet)$_{ppm}$.

REFERENCE EXAMPLE 6

Preparation of
2-oxa-3-oxo-6-syn-(3α-hydroxy-4(R)-methyl octyl)-7-anti-hydroxy-cis-bicyclo[3,3,0]octane 22.5 g. of 2-oxa-3-oxo-6-syn-(3α-hydroxy-4(R)-methyloct-1-enyl)-7-anti-hydroxy-cis-bicyclo[3,3,0]octane dissolved in 230 ml. of ethanol was subjected to catalytic reduction in the presence of 2.3 g. of 5% palladium on charcoal at 20°C. under normal pressure. The catalyst was removed by filtration, the filtrate concentrated under reduced pressure, and the residue subjected to column chromatography with silica gel using benzene-ethanol (20:1) as eluent to obtain 15.2 g. (66.9%) of the desired product as a colourless oil. IR absorption spectrum (liquid film): 3380, 2935, 2860, 1765, 1460, 1370, 1240, 1190, 1045 cm$^{-1}$; NMR spectrum (in CDCl$_3$, TMS as internal standard): δ: 0.75 – 1.05 (6H, multiplet)$_{ppm}$, 1.05 – 3.0 (17H, multiplet)$_{ppm}$, 3.0 – 3.3 (2H, OH), 3,35 – 3.75 (1H, multiplet)$_{ppm}$, 3.75 – 4.20 (1H, multiplet)$_{ppm}$, 4.75 – 5.20 (1H, multiplet)$_{ppm}$.

REFERENCE EXAMPLE 7

Preparation of
2-oxa-3-oxo-6-syn-(3α-hydroxy-4,4-dimethyl-octyl)-7-anti-hydroxy-cis-bicyclo[3,3,0]-octane From 18.6 g. of 2-oxa-3-oxo-6-syn-(3α-hydroxy-4,4-dimethyloct-1-enyl)-7-anti-hydroxy-cis-bicyclo-[3,3,0]octane the desired product was obtained in a yield of 10.4 g. (55.5%) using the method described in Reference Example 6. IR absorption spectrum (liquid film): 3400, 2940 – 2855, 1765, 1465, 1370, 1240, 1190, 1045 cm$^{-1}$; NMR spectrum (in CDCl$_3$, TMS as internal standard): δ0.70 – 1.05 (9H, multiplet)$_{ppm}$, 1.05 – 2.95 (16H, multiplet)$_{ppm}$, 3.2 – 3.8 (3H, multiplet and OH)$_{ppm}$, 3.8 – 4.25 (1H, multiplet)$_{ppm}$, 4.82 – 5.30 (1H, multiplet)$_{ppm}$.

REFERENCE EXAMPLE 8

Preparation of
2-oxa-3-oxo-6-syn-(3α-hydroxy-4(ξ)-ethyloctyl)-7-anti-hydroxy-cis-bicyclo[3,3,0]octane From 18.2 g. of 2-oxa-3-oxo-6-syn-(3α-hydroxy-4(ξ)-ethyloct-1-enyl)-7-anti-hydroxy-cis-bicyclo[3,3,0]-octane the desired product was obtained in a yield of 9.3 g. (50.7%) using the method described in Reference Example 6. IR absorption spectrum (liquid film): 3420, 2945, 2860, 1770, 1465, 1370, 1245, 1195, 1050 cm$^{-1}$; NMR spectrum (in CDCl$_3$, TMS as internal standard): δ: 0.90 (6H, triplet)$_{ppm}$, 1.05 – 2.95 (19H, multiplet)$_{ppm}$, 2.8 – 3.2 (2H, OH), 3.25 – 3.75 (1H, multiplet)$_{ppm}$, 3.75 – 4.25 (1H, multiplet)$_{ppm}$, 4.75 – 5.20 (1H, multiplet)$_{ppm}$.

REFERENCE EXAMPLE 9

Preparation of
2-oxa-3-oxo-6-syn-(3α-hydroxy-5(ξ)-methyl-octyl)-7-anti-hydroxy-cis-bicyclo[3,3,0]octane From 16.7 g. of 2-oxa-3-oxo-6-syn-(3α-hydroxy-5(ξ)-methyloct-1-enyl)-7-anti-hydroxy-cis-bicyclo[3,3,0]octane the desired product was obtained in a yield of 8.9 g. (52.8%) using the method described in Reference Example 6. IR absorption spectrum (liquid film): 3400, 2935, 2850, 1765, 1460, 1370, 1245, 1190, 1045 cm$^{-1}$; NMR spectrum (in CDCl$_3$, TMS as internal standard): δ: 0.75 – 1.05 (6H, multiplet)$_{ppm}$, 1.05 – 3.0 (17H multiplet)$_{ppm}$, 3.3 – 3.8 (3H, multiplet & OH)$_{ppm}$, 3.8 – 4.32 (1H, multiplet)$_{ppm}$, 4.85 – 5.28 (1H, multiplet)$_{ppm}$.

REFERENCE EXAMPLE 10

Preparation of
2-oxa-3-oxo-6-syn-(3α-hydroxy-6(ξ)-methyl-octyl)-7-anti-hydroxy-cis-bicyclo[3,3,0]octane From 21.6 g. of 2-oxa-3-oxo-6-syn-(3α-hydroxy-6(ξ)-methyloct-1-enyl)-7-anti-hydroxy-cis-bicyclo[3,3,0]octane the desired product in the form of an oil was obtained in a yield of 12.4 g. (57.0%) using the method described in Reference Example 6. IR absorption spectrum (liquid film): 3400, 2930, 2850, 1760, 1460, 1415, 1370, 1245, 1190, 1050 cm$^{-1}$; NMR spectrum (in CDCl$_3$, TMS as internal standard): δ: 0.75 – 1.02 (6H, multiplet)$_{ppm}$, 1.05 – 3.05 (17H, multiplet)$_{ppm}$, 2.8 – 3.2 (2H, OH), 3.35 – 3.75 (1H, multiplet)$_{ppm}$, 3.75 – 4.20 (1H, multiplet)$_{ppm}$, 4.82 – 5.26 (1H, multiplet)$_{ppm}$.

REFERENCE EXAMPLE 11

Preparation of
2-oxa-3-oxo-6-syn-(3α-hydroxy-7(ξ)-methyl-octyl)-7-anti-hydroxy-cis-bicyclo[3,3,0]octane From 15.4 g. of 2-oxa-3-oxo-6-syn-(3α-hydroxy-7(ξ)-methyloct-1-enyl)-7-anti-hydroxy-cis-bicyclo[3,3,0]-octane the desired product in the form of an oil was obtained in a yield of 9.5 g. (61.2%) using the method described in Reference Example 6. IR absorption spectrum (liquid film): 3400, 2930, 2850, 1760, 1460, 1415, 1370, 1240, 1185, 1045 cm$^{-1}$; NMR spectrum (in CDCl$_3$, TMS as internal standard): δ: 0.89 (6H, doublet)$_{ppm}$, 1.05 – 3.1 (17H, multiplet)$_{ppm}$, 3.2 – 3.8 (3H, multiplet & OH)$_{ppm}$, 3.8 – 4.30 (1H, multiplet)$_{ppm}$, 4.80 – 5.25 (1H, multiplet)$_{ppm}$.

REFERENCE EXAMPLE 12

Preparation of
2-oxa-3-oxo-6-syn-(3ξ-hydroxy-3(ξ)-methyl-octyl)-7-anti-hydroxy-cis-bicyclo[3,3,0]octane From 15.9 g. of 2-oxa-3-oxo-6-syn-(3ξ-hydroxy-3(ξ)-methyloct-1-enyl)-7-anti-hydroxy-cis-bicyclo-[3,3,0]octane 9.2 g. (57.3%) of the desired product was obtained as an oil using the method described in Reference Example 6. IR absorption spectrum (liquid film): 3380, 2935, 2855, 1765, 1460, 1375, 1240, 1180, 1040 cm$^{-1}$; NMR spectrum (in CDCl$_3$, TMS as internal standard): δ: 0.91 (3H, triplet)$_{ppm}$, 1.0 – 3.05 (21H, multiplet)$_{ppm}$, 3.0 – 3.4 (2H, OH), 3.78 – 4.22 (1H, multiplet)$_{ppm}$, 4.75 – 5.20 (1H, multiplet)$_{ppm}$.

REFERENCE EXAMPLE 13

Preparation of 2-oxa-3-oxo-6-syn-(3ξ-hydroxy-3(ξ), 4(R)-dimethyl-octyl)-7-anti-hydroxy-cis-bicyclo[3,3,0]-octane From 14.3 g. of 2-oxa-3-oxo-6-syn-(3ξ-hydroxy-3(ξ),4(R)-dimethyloct-1-enyl)-7-anti-hydroxy-cis-bicyclo[3,3,0]octane 7.4 g. (51.3%) of the desired product was obtained as a colourless oil using the method described in Reference Example 6. IR absorption spectrum (liquid film): 3400, 2940, 2855, 1770, 1460, 1365, 1240, 1185, 1045 cm$^{-1}$; NMR spectrum (in CDCl$_3$, TMS as internal standard): δ: 0.7 – 1.05 (6H, multiplet)$_{ppm}$, 1.05 – 3.0 (20H, multiplet)$_{ppm}$, 3.1 – 3.5 (2H, OH)$_{ppm}$, 3.80 – 4.25 (1H, multiplet)$_{ppm}$, 4.85 – 5.22 (1H, multiplet)$_{ppm}$.

REFERENCE EXAMPLE 14

Preparation of
2-oxa-3-oxo-6-syn-(3ξ-hydroxy-4(ξ)-phenyl-pentyl)-7-anti-hydroxy-cis-bicyclo[3,3,0]octane 17.2 g. of 2oxa-3-oxo-6-syn-3ξ-hydroxy-4(ξ)-phenyl-pent-1-enyl)-7-anti-hydroxy-cis-bicyclo[3,3,0]-octane dissolved in 170 ml. of ethanol was subjected to catalytic reduction in the presence of 2.1 g. of 5% palladium on charcoal at normal temperature and pressure. After completion of the reaction, the catalyst was removed by filtration, the filtrate concentrated under reduced pressure, and the residue subjected to column chromatography with 350 g. of silica gel using benzene-ethanol (15:1) as eluent to obtain 10.5 g. (60.6%) of the desired product as a colourless oil. IR absorption spectrum (liquid film): 3400, 3030, 2955, 1760, 1605, 1445, 1370, 1240, 1175, 1040 cm$^{-1}$; NMR spectrum (in CDCl$_3$, TMS as internal standard): δ: 1.05 – 3.2 (14H, multiplet)$_{ppm}$, 3.2 – 3.8 (3H, multiplet & OH)$_{ppm}$, 3.8 – 4.25 (1H, multiplet)$_{ppm}$, 4.85 – 5.30 (1H, multiplet), 7.1 – 7.5 (5H, multiplet).

REFERENCE EXAMPLE 15

Preparation of
2-oxa-3-oxo-6-syn-(3α-hydroxy-4(ξ)-cyclohexyl-pentyl)-7-anti-hydroxy-cis-bicyclo[3,3,0]octane The desired product was obtained in a yield of 12.4 g. (63.2%) as a colourless oil from 19.5 g. of 2-oxa-3-oxo-6-syn-(3α-hydroxy-4(ξ)-cyclohexylpent-1-enyl)-7-anti-hydroxy-cis-bicyclo[3,3,0]octane using the same method as described in Reference Example 14. IR absorption spectrum (liquid film): 3400, 2935, 2850, 1765, 1460, 1370, 1240, 1180, 1045 cm$^{-1}$; NMR spectrum (in CDCl$_3$, TMS as internal standard): δ: 0.6 – 1.05 (3H, multiplet)$_{ppm}$, 1.05 – 3.3 (24H, multiplet A OH)$_{ppm}$, 3.38 – 3.8 (1H, multiplet)$_{ppm}$, 3.8 – 4.25 (1H, multiplet)$_{ppm}$, 4.75 – 5.2 (1H, multiplet)$_{ppm}$.

REFERENCE EXAMPLE 16

Preparation of
2-oxa-3-oxo-6-syn-(3ξ-hydroxy-4(ξ)-cyclopentylbutyl)-7-anti-hydroxy-cis-bicyclo-[3,3,0]octane From 16.8 g. of 2-oxa-3-oxo-6-syn-(3ξ-hydroxy-4(ξ)-cyclopentylbut-1-enyl)-7-anti-hydroxy-cis-bicyclo-[3,3,0]octane the desired product was obtained in a yield of 11.5 g. (67.9%) as an oil using the method described in Reference Example 14. IR absorption spectrum (liquid film): 3380, 2940, 2855, 1765, 1460, 1370, 1240, 1180, 1045 cm$^{-1}$; NMR spectrum (in CDCl$_3$, TMS as internal standard): δ: 1.0 – 3.05 (21H, multiplet)$_{ppm}$, 3.1 – 3.4 (2H, OH), 3.40 – 3.8 (1H, multiplet)$_{ppm}$, 3.8 – 4.30 (1H, multiplet)$_{ppm}$, 4.85 – 5.30 (1H, multiplet)$_{ppm}$,

REFERENCE EXAMPLE 17

Preparation of
2-oxa-3-oxo-6-syn-(3ξ-hydroxy-4(ξ)-cyclopentyl-pentyl)-7-anti-hydroxy-cis-bicyclo-[3,3,0]octane From 6.2 g. of 2-oxa-3-oxo-6-syn-(3ξ-hydroxy-4(ξ)-cyclopentylpent-1-enyl)-7-anti-hydroxy-cis-bicyclo[3,3,0]octane the desired product was obtained in a yield of 5.82 g. (93.9%) as an oil using the method described in Reference Example 5. IR absorption spectrum (liquid film): 3440, 2940, 2850, 1770, 1460, 1380, 1200, 1095, 1075, 1030 cm$^{-1}$; NMR spectrum (in CDCl$_3$ TMS as internal standard): δ: 0.07~0.98 (3H, doublet) 3.30~3.80 (2H, broad singlet) 3.80~4.30 (2H, multiplet) 4.73~5.22 (1H, multiplet).

REFERENCE EXAMPLE 18

Preparation of
2-oxa-3-oxo-6syn-(3α-tetrahydropyranyloxy-decyl)-7-anti-tetrahydropyranyloxy-cis-bicyclo[3,3,0]octane 14.6 g. of 2-oxa-3-oxo-6-syn-(3α-hydroxydecyl)-7-anti-hydroxy-cis-bicyclo[3,3,0]octane [prepared as described in Reference Example 4] were dissolved in 150 ml. of methylene chloride, and to the resulting solution was added 11.6 g. of 2,3-dihydropyran and 150 mg. of p-toluenesulphonic acid. After reaction at 25°C. for 15 minutes with stirring, a small amount of pyridine was added to stop the reaction. The reaction mixture was extracted with ethyl acetate after addition of an approximately 50% saturated aqueous sodium chloride solution, the organic layer was treated with further saturated aqueous sodium chloride, dried and concentrated to obtain 22.5 g. (yield quantitative) of the desired product as an oil. IR absorption spectrum (liquid film): 2940, 2860, 1775, 1470 – 1445, 1380, 1360, 1240, 1165, 1135, 1080, 1040, 1025 cm$^{-1}$; NMR spectrum (in CDCl$_3$, TMS as internal standard): δ: 0.90 (3H, triplet)$_{ppm}$, 1.05 – 3.2 (34H, multiplet)$_{ppm}$, 3.2 – 4.25 (6H, multiplet)$_{ppm}$, 4.4 – 4.75 (2H, multiplet)$_{ppm}$, 4.75 – 5.20 (1H, multiplet)$_{ppm}$.

REFERENCE EXAMPLE 19

Preparation of
2-oxa-3-oxo-6-syn-(3α-tetrahydropyranyloxy-4(R)-methyl-octyl)-7-anti-tetrahydro-pyranyloxy-cis-bicyclo[3,3,0]octane 14.7 g. of 2-oxa-3-oxo-6-syn-(3α-hydroxy-4(R)-methyl-octyl)-7-anti-hydroxy-cis-bicyclo[3,3,0]octane [prepared as described in Reference Example 6] were dissolved in 150 ml. of methylene chloride, and to the resulting solution were added 11.8 g. of 2,3-dihydropyran and a small amount of p-toluenesulphonic acid. After reaction at room temperature for 15 minutes with stirring, a small amount of pyridine was added to stop the reaction. The reaction mixture was extracted with diethyl ether after addition of an approximately 50% saturated aqueous sodium chloride solution, the organic layer was treated with further saturated aqueous sodium chloride, dried and concentrated to obtain 23.0 g. (98.5%) of the desired product as an oil. IR absorption spectrum (liquid film): 2935, 2835, 1770, 1470, – 1440, 1380, 1240, 1160, 1135, 1080, 1040, 1025 cm$^{-1}$; NMR spectrum (in CDCl$_3$, TMS as internal standard): δ: 0.75 – 1.05 (6H multiplet)$_{ppm}$, 1.05 – 3.2 (29H, multiplet)$_{ppm}$, 3.25 – 4.3 (6H, multiplet)$_{ppm}$, 4.4 – 4.75 (2H, multiplet), 4.75 – 5.20 (1H, multiplet).

By the same method as described in Reference examples 18 and 19, the following compounds were prepared: 2-oxa-3-oxo-6-syn-(3α-tetrahydropyranyloxyheptyl)-7-anti-tetrahydropyranyloxy-cis-bicyclo[3,3,-0]octane, 2-oxa-3-oxo-6-syn-(3α-tetrahydropyranyloxy-4,4-dimethyl-octyl)-7-anti-tetrahydropyranyloxy-cis-bicyclo[3,3,0]octane, 2-oxa-3-oxo-6-syn-(3α-tetrahydropyranyloxy-4(ξ)-ethyl-octyl)-7-anti-tetrahydropyranyloxy-cis-bicyclo-[3,3,0]octane, 2-oxa-3-oxo-6-syn-(3α-tetrahydropyranyloxy-5(ξ)-methyl-octyl)-7-anti-tetrahydropyranyloxy-cis-bicyclo[3,3,0]octane, 2-oxa-3-oxo-6-syn-(3α-tetrahydropyranyloxy-6(ξ)-methyl-octyl)-7-anti-tetrahydropyranyloxy-cis-bicyclo[3,3,0]octane, and 2-oxa-3oxo-6-syn-(3α-tetrahydropyranyloxy-7(ξ)-methyl-octyl)-7-anti-tetrahydropyranyloxy-cis-bicyclo[3,3,0]octane.

REFERENCE EXAMPLE 20

Preparation of
2-oxa-3-oxo-6-syn-(3ξ-tetrahydropyranyloxy-3(ξ)-methyl-octyl)-7-anti-tetrahydropyranyloxy-cis-bicyclo[3,3,0]octane 8.9 g. of 2-oxa-3-oxo-6-syn-(3ξ-hydroxy-3(ξ)-methyl-octyl)-7-anti-hydroxy-cis-bicyclo[3,3,0]octane [prepared as described in Reference Example 12] were dissolved in 85 ml. of methylene chloride. To the resulting solution 7.1 g. of 2,3-dihydropyran and 80 mg. of p-toluenesulphonic acid were added and the reaction mixture was left at room temperature for 15 minutes. The reaction mixture was then worked up as described in Reference Example 19 to obtain 13.9 g. (96.7%) of the desired product as a light yellow oil. IR absorption spectrum (liquid film): 2945, 2860, 1775, 1470, – 1440, 1380, 1245, 1165, 1140, 1085, 1045, 1130 cm$^{-1}$; NMR spectrum (in CDCl$_3$, TMS as internal standard): δ: 0.89 (3H, triplet)$_{ppm}$, 1.05 – 3.2 (33H, multiplet)$_{ppm}$, 3.5 – 4.25 (5H, multiplet), 4.35 – 4.75 (2H, multiplet)$_{ppm}$, 4.75 – 5.20 (1H, multiplet)$_{ppm}$.

REFERENCE EXAMPLE 21

Preparation of
2-oxa-3-oxo-6-syn-(3α-tetrahydropyranyloxy-3(ξ), 4(R)-dimethyl-octyl)-7-anti-tetrahydropyranyloxy-cis-bicyclo[3,3,0]octane To a solution of 7.0 g. of 2-oxa-3-oxo-6-syn-(3ξ-hydroxy-3(ξ),4(R)-dimethyl-octyl)-7-anti-hydroxy-cis-bicyclo[3,3,0]octane [prepared as described in Reference Example 13] dissolved in 70 ml. of methylene chloride there were added 5.6 g. of 2,3-dihydropyran and 70 mg. of p-toluenesulphonic acid. The reaction was allowed to proceed at 20°–25°C. for 15 minutes. Working-up of the reaction mixture as described in Reference Example 19 gave 10.6 g. (97%) of the desired product as an oil. IR absorption spectrum (liquid film): 2940, 2870, 1775, 1470 – 1450, 1380, 1240, 1165, 1135, 1080, 1040, 1025 cm$^{-1}$; NMR spectrum (in CDCl$_3$, TMS as internal standard): δ: 0.75 – 1.05 (6H, multiplet)$_{ppm}$, 1.05 – 3.2 (32H, multiplet)$_{ppm}$, 3.5 – 4.25 (5H, multiplet)$_{ppm}$, 4.3 – 4.75 (2H, multiplet)$_{ppm}$, 4.75 – 5.20 (1H, multiplet)$_{ppm}$.

REFERENCE EXAMPLE 22 preparation of 2-oxa-3-oxo-6-syn-(3α-tetrahydropyranyloxy-4(ξ)-cyclohexy-pentyl)-7-anti-tetrahydropyranyloxy-cis-bicyclo[3,3,0]octane 12.0 g. of 2-oxa-3-oxo-6-syn-(3α-hydroxy-4(ξ)-cyclohexyl-pentyl)-7-anti-hydroxy-cis-bicyclo-[3,3,0]octane [prepared as described in Reference Example 15] were dissolved in 150 ml. of methylene chloride, and to the resulting solution there were added 9.2 g. of 2,3-dihydropyran and 120 mg. of p-toluenesulphonic acid. The reaction mixture was left at 20°C. for 15 minutes with stirring. A small amount of pyridine was then added to stop the reaction. The reaction mixture was extracted with ethyl acetate after addition of an approximately 50% saturated aqueous sodium chloride solution, the organic layer was treated with further saturated aqueous sodium chloride, dried and concentrated to obtain 18.0 g. of the desired product as an oil. IR absorption spectrum (liquid film): 2940, 2860, 1780, 1470 – 1450, 1380, 1240, 1165, 1135, 1080, 1040, 1025 cm$^{-1}$; NMR spectrum (in CDCl$_3$, TMS as internal standard): δ: 0.55 – 1.0 (3H, multiplet)$_{ppm}$, 1.05 – 3.2 (34H, multiplet)$_{ppm}$, 3.3 – 4.3 (6H, multiplet)$_{ppm}$, 4.3 – 4.75 (2H, multiplet)$_{ppm}$, 4.75 – 5.25 (1H, multiplet)$_{ppm}$.

In a similar manner there were prepared 2-oxa-3-oxo-6-syn-(3ξ-tetrahydropyranyloxy-4(ξ)-phenyl-pentyl)-7-anti-tetrahydropyranyloxy-cis-bicyclo[3,3,0]octane and 2-oxa-3-oxo-6-syn-(3ξ-tetrahydropyranyloxy-4(ξ)-cyclopentylbutyl)-7-anti-tetrahydropyranyloxy-cis-bicyclo[3,3,0]octane.

REFERENCE EXAMPLE 23

Preparation of 2-oxa-3-oxo-6-syn-(3ξ-tetrahydropyranyloxy-4(ξ)-cyclopentyl-pentyl)-7-anti-tetrahydropyranyloxy-cis-bicyclo[3,3,0]octane 4.8 g. of 2-oxa-3-oxo-6-syn-(3ξ-hydroxy-4(ξ)-cyclopentyl-pentyl)-7-anti-hydroxy-cis-bicyclo[3,3,0]octane were dissolved in 48 ml. of methylene chloride and to the resulting solution were added 4.8 ml. of 2,3-dihydropyran and 25 mg. of p-toluenesulphonic acid and the reaction mixture was allowed to react at 20°C. for 15 minutes with stirring. The reaction mixture was then extracted with ethyl acetate after addition of a 50% saturated aqueous sodium chloride solution, the organic layer was treated with further saturated aqueous sodium chloride solution, dried over magnesium chloride, and concentrated to obtain 7.35 g. of the desired product as an oil. IR absorption spectrum (liquid film): 2930, 2850, 1770, 1450, 1355, 1240, 1180, 1120, 1080, 1035, 1025 cm$^{-1}$; NMR spectrum (in CDCl$_3$, TMS as internal standard): δ: 0.70~1.00 (3H, doublet), 4.46~4.84 (2H, multiplet), 4.84~5.20 (1H, multiplet).

REFERENCE EXAMPLE 24

Preparation of 2-oxa-3-hydroxy-6-syn-(3α-tetrahydropyranyloxy-decyl)-7-anti-tetrahydropyranyloxy-cis-bicyclo[3,3,0]octane 22.0 g. of 2-oxa-3-oxo-6-syn-(3α-tetrahydropyranyloxy-decyl)-7-anti-tetrahydropyranyloxy-cis-bicyclo-[3,3,0]octane [prepared as described in Reference Example 18] were dissolved in 440 ml. of toluene and cooled to −60°C. To the solution was added dropwise with stirring, over a period of 30 minutes, a solution containing 25 g. of diisobutylaluminium hydride in 100 ml. of toluene. The reaction mixture was stirred for a further 15 minutes at the same temperature and then methanol was added to decompose the excess of the hydride until the evolution of hydrogen ceased. Stirring was continued for a short time whilst the temperature was allowed to rise to room temperature, and then an approximately 50% saturated aqueous sodium chloride solution was added, the organic layer was separated and the aqueous layer extracted several times with ethyl acetate. The organic layers were combined, treated with aqueous sodium chloride solution, dried and concentrated in vacuo to obtain 21.3 g. of the desired product as an oil. IR absorption spectrum (liquid film): 3420, 2945, 2860, 1450, 1360, 1200, 1130, 1080, 1025 cm$^{-1}$; NMR spectrum (in CDCl$_3$, TMS as internal standard): δ: 0.88 (3H, triplet)$_{ppm}$, 1.05 – 2.8 (34H, multiplet)$_{ppm}$, 3.3–4.25 (7H, multiplet)$_{ppm}$, 4.3 – 4.85 (3H, multiplet)$_{ppm}$, 5.45 – 5.75 (1H, OH).

REFERENCE EXAMPLE 25

By the method described in Reference Example 24, 2-oxa-3-hydroxy-6-syn-(3α-tetrahydropyranyloxyheptyl)-7-anti-tetrahydropyranyloxy-cis-bicyclo-[3,3,0]octane was obtained as an oil, starting from the corresponding 3-oxo compound (cf. Reference Example 19). IR absorption spectrum (liquid film): 3400, 2950, 2865, 1450, 1365, 1205, 1130, 1085, 1030 cm$^{-1}$; NMR spectrum (in CDCl$_3$, TMS as internal standard): δ: 0.89 (3H, triplet)$_{ppm}$, 1.05 – 2.8 (28H, multiplet)$_{ppm}$, 3.3 – 4.3 (7H, multiplet)$_{ppm}$, 4.3 – 4.85 (3H, multiplet)$_{ppm}$, 5.40 – 5.70 (1H, OH).

REFERENCE EXAMPLE 26

By the same method described in Reference Example 24, 2-oxa-3-hydroxy-6-syn-(3ξ-tetrahydropyranyloxy-4,4-dimethyl-octyl)-7-anti-tetrahydropyranyloxy-cis-bicyclo[3,3,0]octane was obtained starting from the corresponding 3-oxo compound (cf. Reference Example 19); the product was an oil. IR absorption sepctrum (liquid film): 3400, 2940, 2865, 1450, 1360, 1200, 1130, 1080, 1025 cm$^{-1}$; NMR spectrum (in CDCl$_3$, TMS as internal standard): δ: 0.75 – 1.05 (9H, multiplet)$_{ppm}$, 1.05 – 2.85 (28H, multiplet)$_{ppm}$, 3.25 – 4.25 (7H, multiplet)$_{ppm}$, 4.3 – 4.85 (3H, multiplet)$_{ppm}$, 5.40 – 5.70 (1H, OH).

REFERENCE EXAMPLE 27

16.9 g. of 2-oxa-3-hydroxy-6-syn-(3ξ-tetrahydropyranyloxy-6(ξ)-methyl-octyl)-7-anti-tetrahydropyranyloxy-cis-bicyclo[3,3,0]octane was obtained as an oil following the same method as described in Reference Example 24 from 18.1 g. of 2-oxa-3-oxo-6- syn-(3α-tetrahydropyranyloxy-6(ξ)-methyl-octyl)-7-anti-tetrahydropyranyloxy-cis-bicyclo[3,3,0]octane.
IR absorption spectrum (liquid film): 3380, 2945, 2870, 1450, 1360, 1200, 1130, 1080, 1025 cm$^{-1}$; NMR spectrum (in CDCl$_3$, TMS as internal standard): δ: 0.75 – 1.05 (6H, multiplet)$_{ppm}$, 1.05 – 2.8 (29H, multiplet)$_{ppm}$, 3.30 – 4.25 (7H, multiplet)$_{ppm}$, 4.25 – 4.85 (multiplet)$_{ppm}$, 5.45 – 5.75 (1H, OH).

REFERENCE EXAMPLE 28

By the method described in Reference Example 24, 2-oxa-3-hydroxy-6-syn-(3α-tetrahydropyranyloxy-4(ξ)-phenyl-pentyl)-7-anti-tetrahydropyranyloxy-cis-bicyclo-[3,3,0]octane was obtained as an oil, starting from the corresponding 3-oxo compound (cf. Reference Example 22). IR absorption spectrum (liquid film): 3400, 3020, 2920, 2855, 1600, 1445, 1355, 1200, 1125, 1020 cm$^{-1}$; NMR spectrum (in CDCl$_3$, TMS as internal standard): δ: 1.0 – 2.95 (26H, multiplet), 3.25 – 4.3 (7H, multiplet)$_{ppm}$, 4.3 – 4.85 (3H, multiplet)$_{ppm}$, 5.40 – 5.70 (1H, OH), 7.05 – 7.45 (5H, multiplet).

REFERENCE EXAMPLE 29

By the method described in Reference Example 24, 2-oxa-3-hydroxy-6-syn-(3α-tetrahydropyranyloxy-4(ξ)-cyclopentyl-butyl)-7-anti-tetrahydropyranyloxy-cis-bicyclo[3,3,0]octane was obtained as an oil, starting from the corresponding 3-oxo compound (cf. Reference Example 22). IR absorption spectrum (liquid film): 3400, 2950, 1450, 1380, 1360, 1205, 1130, 1080, 1025 cm$^{-1}$; NMR spectrum (in CDCl$_3$, TMS as internal standard): δ: 1.05 – 2.85 (33H, multiplet)$_{ppm}$, 3.3 – 4.3 (7H, multiplet)$_{ppm}$, 4.3 – 4.85 (3H, multiplet)$_{ppm}$, 5.35 – 5.65 (1H, OH).

By the same method as described in Reference Example 24 the following compounds were prepared from the corresponding 3-oxo compounds:

2-oxa-3-hydroxy-6-syn-(3α-tetrahydropyranyloxy-4(R)-methyl-octyl)-7-anti-tetrahydropyranyloxy-cis-bicyclo[3,3,0]octane, 2-oxa-3-hydroxy-6-syn-(3α-tetrahydropyranyloxy-4(ξ)-ethyl-octyl)-7-anti-tetrahydropyranyloxy-cis-bicyclo[3,3,0]octane, 2-oxa-3-hydroxy-6-syn-(3α-tetrahydropyranyloxy-5(ξ)-methyl-octyl)-7-anti-tetrahydropyranyloxy-cis-bicyclo[3,3,0]octane, 2-oxa-3-hydroxy-6-syn-(3α-tetrahydropyranyloxy-7(ξ)-methyl-octyl-7-anti-tetrahydropyranyloxy-cis-bicyclo[3,3,0]octane, 2-oxa-3-hydroxy-6-syn-(3ξ-tetrahydropyranyloxy-3(ξ)-methyl-octyl)-7-anti-tetrahydropyranyloxy-cis-bicyclo[3,3,0]octane, 2-oxa-3-hydroxy-6-syn-(3ξ-tetrahydropyranyloxy-3(ξ), 4(R)-dimethyl-octyl)-7-anti-tetrahydropyranyloxy-cis-bicyclo[3,3,0]octane, and 2-oxa-3-hydroxy-6-syn-(3α-tetrahydropyranyloxy-4(ξ)-cyclohexyl-pentyl)-7-anti-tetrahydropyranyloxy-cis-bicyclo[3,3,0]octane.

REFERENCE EXAMPLE 30

Preparation of 2-oxa-3-hydroxy-6-syn-(3ξ-tetrahydropyranyloxy-4(ξ)-cyclopentyl-pentyl)-7-anti-tetrahydropyranyloxy-cis-bicyclo[3,3,0]octane 7.3 g. of 2-oxa-3-oxo-6-syn-(3ξ-tetrahydropyranyloxy-4(ξ)-cyclopentyl-pentyl)-7-anti-tetrahydropyranyloxy-cis-bicyclo-[3,3,0]octane [prepared as described in Reference Example 23] were dissolved in 75 ml. of toluene and cooled to −60°C. To the solution was added dropwise with stirring 6.4 g. of diisobutylaluminium hydride in 25 ml. of toluene over a period of 30 minutes. The reaction mixture was stirred for a further 15 minutes at the same temperature, and then methanol was added to decompose the excess of the hydride until the evolution of hydrogen ceased. Stirring was continued for a short time, the temperature was allowed to rise to room temperature and an approximately 50% saturated aqueous sodium chloride solution was added. The organic layer was separated, and the aqueous layer was extracted several times with ethyl acetate. The organic layer was treated with aqueous sodium chloride solution, dried and concentrated in vacuo to obtain 6.62 g. (90.0%) of the desired product as an oil. IR absorption spectrum (liquid film): 3400, 2930, 2860, 1440, 1355, 1260, 1200, 1120, 1080, 1035, 1025 cm$^{-1}$; NMR spectrum (in CDCl$_3$, TMS as internal standard): δ: 0.70~1.03 (3H, doublet), 3.25~4.20 (6H, multiplet), 4.40~4.85 (3H, multiplet), 5.4~5.7 (1H, multiplet).

EXAMPLE 4

Preparation of 9α-hydroxy-11α,15α-ditetrahydropyranyloxy-ω-bis-homoprost-cis-5-enoic acid.

8.55 g. of sodium hydride (55% content) were dissolved in 105 ml. of dimethylsulphoxide with stirring and the reaction mixture heated at 65°–70°C. for about 1 hour until no more effervescence occurred. After cooling the resulting solution containing sodiomethylsulphinylcarbanide to room temperature, it was added dropwise to a solution of 46.2 g. of 4-carboxy-n-butyl-triphenylphosphonium bromide in 90 ml. of dimethyl-sulphoxide at a temperature of 20°–25°C.; the reaction mixture turned red.

To the solution was added a solution of 46.2 g. of 2-oxa-3-hydroxy-6-syn-(3α-tetrahydropyranyloxydecyl)-7-anti-tetrahydropyranyloxy-cis-bicyclo[3,3,0]-octane [prepared as described in Reference Example 24] in 90 ml. of dimethylsulphoxide, and the mixture stirred at room temperature for 2 hours. The reaction mixture was then poured into about 1 liter of ice-water and extracted with a mixed solvent comprising ethyl acetate and diethyl ether (1:1) to remove any neutral matter, and then extracted again, after acidification with oxalic acid to pH 2, with a mixture of pentane and diethyl ether (1:1). The extract was washed consecutively with water and aqueous sodium chloride solution, dried and concentrated. The residue after concentration was subjected to purification by silica gel column chromatography using benzene – ethanol (20:1) as eluent to give 12.6 g. (54.5%) of the desired product as a colourless oil. IR absorption spectrum (liquid film): 3420, 2940, 2860, 2700 – 2350, 1710, 1450, 1440, 1355, 1240, 1205, 1135, 1085, 1030 cm$^{-1}$; NMR spectrum (in CDCl$_3$, TMS as internal standard): δ: 0.90 (3H, triplet), 1.05 – 2.65 (40H, multiplet), 3.35 – 4.3 (7H, multiplet), 4.4 – 4.7 (2H, multiplet), 4.7 – 5.2 (2H, broad peak) 5.25 – 5.65 (2H, multiplet)$_{ppm}$.

EXAMPLE 5

Preparation of 9α-hydroxy-11α,15α-ditetrahydropyranyloxy-ω-nor-prost-cis-5-enoic acid To a solution of 42.3 g. of 4-carboxy-n-butyltriphenylphosphonium bromide in 85 ml. of dimethylsulphoxide was added at about 25°C. a solution of sodiomethylsulphinylcarbanide prepared from 7.87 g. of sodium hydride (55% content) and 95 ml. of dimethylsulphoxide and the reaction mixture was stirred for 5 minutes. A solution of 16.3 g. of 2-oxa-3-hydroxy-6-syn-(3α-tetrahydropyranyloxy-heptyl)-7-anti-tetrahydropyranyloxy-cis-bicyclo[3,3,0]octane [prepared as described in Reference Example 25] in 70 ml. of dimethylsulphoxide was then added, and stirring continued for 2 hours at room temperature. After completion of the reaction, the reaction mixture was worked up in the same way as described in Example 4 and the product purified by column chromatography to give 9.9 g. (50.7%) of the desired product as a colourless oil. IR absorption spectrum (liquid film): 3430, 2945, 2860, 2700 – 2300 1710, 1440, 1375, 1240, 1135, 1080, 1025 cm$^{-1}$; NMR spectrum (in CDCl$_3$, TMS as internal standard): δ: 0.89 (3H, triplet), 1.05 – 2.6 (34H, multiplet), 3.35 – 4.3 (7H, multiplet), 4.4 – 4.7 (2H, multiplet), 5.1 – 5.65 (4H broad peak and multiplet)$_{ppm}$.

EXAMPLE 6

Preparation of 9α-hydroxy-11α,15α-ditetrahydropyranyloxy-16(R)-methyl-prost-cis-5-enoic acid A solution of sodiomethylsulphinylcarbanide prepared from 9.17 g. of sodium hydride (55% content) in 110 ml. of dimethylsulphoxide was stirred at room temperature for 5 minutes with a solution containing 49.5 g. of 4-carboxy-n-butyl-triphenylphosphonium bromide in dimethylsulphoxide.

21.4 g. of 2-oxa-3-hydroxy-6-syn-(3α-tetrahydropyranyloxy-4(R)-methyl-octyl)-7-anti-tetrahydropyranyloxy-cis-bicyclo[3,3,0]octane [cf. Reference Example 29] in 80 ml. of dimethylsulphoxide was added, and stirring continued for 2 hours at the same temperature to complete the reaction.

Analogous working-up and purification of the product as described in Example 4 gave the desired product as a colourless oil; yield 12.2 g. (48.1%). IR absorption spectrum (liquid film): 3400, 2930, 2855, 2700 – 2400, 1740, 1710, 1440, 1380, 1240, 1135, 1080, 1025 cm$^{-1}$; NMR spectrum (in CDCl$_3$, TMS as internal standard): δ: 0.75 – 1.05 (6H, multiplet), 1.05 – 2.65 (35H, multiplet), 3.4~4.3 (7H, multiplet) 4.35 – 4.7 (2H, multiplet), 4.3 – 5.2 (2H, broad peak), 5.25 – 5.6 (2H, multiplet)$_{ppm}$.

EXAMPLE 7

Preparation of 9α-hydroxy-11α,15α-ditetrahydropyranyloxy-16,16-dimethyl-prost-cis-5-enoic acid To a solution of 35.7 g. of 4-carboxy-n-butyltriphenylphosphonium bromide in 70 ml. of dimethylsulphoxide was added dropwise a solution of sodiomethylsulphinylcarbanide prepared by the method described in Example 4 from 6.60 g. of sodium hydride (55% content) and 80 ml. of dimethylsulphoxide, and the reaction mixture was stirred for 5 minutes.

A solution of 15.1 g. of 2-oxa-3-hydroxy-6-syn-(3α-tetrahydropyranyloxy-4,4-dimethyl-octyl)-7-anti-tetrahydropyranyloxy-cis-bicyclo[3,3,0]octane [prepared as described in Reference Example 26] in 60 ml. of dimethylsulphoxide was added, and stirring continued at room temperature for 2.5 hours to complete the reaction. Usual working-up of the reaction mixture and purification of the crude product as described in Example 4 gave the desired product as a colourless oil; yield 9.2 g. (51.7%). IR absorption spectrum (liquid film): 3450, 2940, 2860, 2700 – 2300, 1740, 1710, 1440, 1380, 1240, 1200, 1130, 1080, 1025 cm$^{-1}$; NMR spectrum (in CDCl$_3$, TMS as internal standard): δ: 0.75 – 1.05 (9H, multiplet), 1.05 – 2.6 (34H, multiplet), 3.35 – 4.25 (7H, multiplet), 4.3 – 4.9 (4H, broad peak and multiplet), 5.25 – 5.65 (2H, multiplet)$_{ppm}$.

EXAMPLE 8

Preparation of 9α-hydroxy-11α,15α-ditetrahydropyranyloxy-16(ξ)-ethyl-prost-cis-5-enoic acid To a solution of 34.3 g. of 4-carboxy-n-butyltriphenylphosphonium bromide in 65 ml. of dimethylsulphoxide was added dropwise a solution of sodiomethylsulphinylcarbanide prepared by the method described in Example 4 from 6.33 g. of sodium hydride (55% content) and 75 ml. of dimethylsulphoxide. A solution of 14.5 g. of 2-oxa-3-hydroxy-6-syn-(3α-tetrahydropyranyloxy-4(ξ)-ethyloctyl)-7-anti-tetrahydropyranyloxy-cis-bicyclo[3,3,0]octane [cf. Reference Example 29] in 58 ml. of dimethylsulphoxide was added, and stirring continued at room temperature for 2 hours to complete the reaction. Usual working-up of the reaction mixture and purification by column chromatography of the crude product gave the desired product as a colourless oil; yield 8.5 g. (47.1%). IR absorption spectrum (liquid film): 3420, 2935, 2855, 2700 – 2400, 1740, 1710, 1440, 1380, 1240, 1135, 1080, 1030 cm$^{-1}$; NMR spectrum (in CDCl$_3$, TMS as internal standard): δ: 0.89 (6H), 1.05 – 2.65 (37H, multiplet), 3.4 – 4.3 (7H, multiplet), 4.4 – 4.7 (2H, multiplet), 5.0 – 5.65 (4H, broad peak and multiplet)$_{ppm}$.

EXAMPLE 9

Preparation of 9α-hydroxy-11α,15α-ditetrahydropyranyloxy-17(ξ)-methyl-prost-cis-5-enoic acid To a solution of 27.5 g. of 4-carboxy-n-butyltriphenylphosphonium bromide in 55 ml. of dimethylsulphoxide was added dropwise a solution of sodiomethylsulphinylcarbanide prepared by the method described in Example 4 from 5.07 g. of sodium hydride (55% content) and 60 ml. of dimethylsulphoxide at 22°–27°C. A solution of 11.3 g. of 2-oxa-3-hydroxy-6-syn-(3α-tetrahydropyranyloxy-5-(ξ)-methyl-octyl)-7-anti-tetrahydropyranyloxy-cis-bicyclo-[3,3,0]octane [cf. Reference Example 29] in 45 ml. of dimethylsulphoxide was added, and stirring continued at room temperature for 2 hours to complete the reaction. Usual working-up of the reaction mixture and purificaton of the crude product gave the desired product as a colourless oil; yield 7.8 g. (58.4%). IR absorption spectrum (liquid film): 3400, 2940, 2860, 2700 – 2300, 1740, 1710, 1450, 1355, 1240, 1135, 1080, 1030 cm$^{-1}$; NMR spectrum (in CDCl$_3$, TMS as internal standard): δ: 0.75 – 1.05 (6H, multiplet), 1.05 – 2.6 (35H, multiplet), 3.35 – 4.35 (7H, multiplet), 4.4 – 4.7 (2H, multiplet), 4.8 – 5.2 (2H, broad peak), 5.28 – 5.65 (2H, multiplet)$_{ppm}$.

EXAMPLE 10

Preparation of 9α-hydroxy-11α,15α-ditetrahydropyranyloxy-18($\xi$)-methyl-prost-cis-5-enoic acid To a solution of 37.4 g. of 4-carboxy-n-butyltriphenylphosphonium bromide in 65 ml. of dimethylsulphoxide was added dropwise a solution of sodiomethylsulphinylcarbanide prepared by the method described in Example 4 from 7.10 g. of sodium hydride (55% content) and 85 ml. of dimethylsulphoxide. A solution of 15.8 g. of 2-oxa-3-hydroxy-6-syn-(3α-tetrahydropyranyloxy-6($\xi$)-methyl-octyl)-7-anti-tetrahydropyranyloxy-cis-bicyclo-[3,3,0]octane [prepared as described in Reference Example 27] in 60 ml. of dimethylsulphoxide was added, and stirring continued at 25°C. for 2 hours to complete the reaction. Usual working-up of the reaction mixture and purification by column chromatography of the crude product gave the desired product as a colourless oil; yield 10.3 g. (55.1%). IR absorption spectrum (liquid film): 3400, 2935, 2855, 2700 – 2350, 1710, 1440, 1380, 1240, 1200, 1135, 1085, 1030 cm$^{-1}$; NMR spectrum (in CDCl$_3$, TMS as internal standard): δ: 0.75 – 1.05 (6H, multiplet), 1.05 – 2.6 (35H, multiplet), 3.4 – 4.3 (7H, multiplet), 4.4 – 4.9 (4H, broad peak, multiplet), 5.25 – 5.63 (2H, multiplet)$_{ppm}$.

EXAMPLE 11

Preparation of 9α-hydroxy-11α,15α-ditetrahydropyranyloxy-19($\xi$)-methyl-prost-cis-5-enoic acid To a solution of 25.3 g. of 4-carboxy-n-butyl-triphenylphosphonium bromide in 50 ml. of dimethylsulphoxide was added dropwise a solution of sodiomethylsulphinylcarbanide prepared by the method described in Example 4 from 4.85 g. of sodium hydride (55% content) and 56 ml of dimethylsulphoxide. A solution of 10.7 g of 2-oxa-3-hydroxy-6-syn-(3α-tetrahydropyranyloxy-7($\xi$)-methyl-octyl)-7-anti-tetrahydropyranyloxy-cis-bicyclo[3,3,0]octane [cf. Reference Example 29] in 40 ml. of dimethylsulphoxide was added, and stirring continued at 25°C. for 2 hours to complete the reaction. Usual working-up of the reaction mixture and purification of the crude product gave the desired product as a colourless oil; yield 7.1 g. (56.0%). IR absorption spectrum (liquid film): 3400, 2950, 2870, 2700 – 2300, 1710, 1450, 1380, 1240, 1205, 1135, 1085, 1030 cm$^{-1}$; NMR spectrum (in CDCl$_3$, TMS as internal standard): δ: 0.89 (6H, doublet), 1.05 – 2.6 (35H, multiplet), 3.3 – 4.3 (7H, multiplet), 4.4 – 4.7 (2H, multiplet), 4.9 – 5.3 (2H, broad peak), 5.3 – 5.65 (2H, multiplet)$_{ppm}$.

EXAMPLE 12

Preparation of 9α-hydroxy-11α,15$\xi$-ditetrahydropyranyloxy-15($\xi$)-methyl-prost-cis-5-enoic acid To a solution of 32.4 g. of 4-carboxy-n-butyltriphenylphosphonium bromide in 65 ml. of dimethylsulphoxide was added dropwise a solution of sodiomethylsulphinylcarbanide prepared by the method described in Example 4 from 5.97 g. of sodium hydride (55% content) and 72 ml. of dimethylsulphoxide at 22°–28°C. After 5 minutes a solution of 13.3 g. of 2-oxa-3-hydroxy-6-syn-(3$\xi$-tetrahydropyranyloxy-3($\xi$)-methyl-octyl)-7-anti-tetrahydropyranyloxy-cis-bicyclo[3,3,0]octane [cf. Reference Example 29] in 50 ml. of dimethylsulphoxide was added, and stirring continued at room temperature for 2 hours to complete the reaction. Usual working-up of the reaction mixture and purification of the crude product gave the desired product as an oil; yield 7.7 g. (48.9%). IR absorption spectrum (liquid film): 3400, 2935, 2850, 2700 – 2400, 1740, 1710, 1440, 1380, 1245, 1205, 1130, 1080, 1025 cm$^{-1}$; NMR spectrum (in CDCl$_3$, TMS as internal standard): δ: 0.90 (3H, triplet), 1.05 – 2.6 (39H, multiplet), 3.5 – 4.3 (6H, multiplet), 4.4 – 4.7 (2H, multiplet), 5.0 – 5.65 (4H, broad peak and multiplet)$_{ppm}$.

EXAMPLE 13

Preparation of 3($\xi$),16($\xi$)-dimethyl-9α-hydroxy-11α,15α-ditetrahydropyranyloxy-prost-cis-5-enoic acid To a solution of 25.7 g. of 4-carboxy-3-methyl-n-butyl-triphenylphosphonium bromide in 50ml. of dimethylsulphoxide was added dropwise a solution of sodiomethylsulphinylcarbanide prepared by the method described in Example 4 from 4.63 g. of sodium hydride (55% content) and 55 ml. of dimethylsulphoxide at 25°C. A solution of 10.5 g. of 2-oxa-3-hydroxy-6-syn-(3α-tetrahydropyranyloxy-4($\xi$)-methyl-octyl)-7-anti-tetrahydropyranyloxy-cis-bicyclo[3,3,0]octane in 40 ml. of dimethylsulphoxide was added, and stirring continued at room temperature for 2.5 hours to complete the reaction. Usual working-up of the reaction mixture and purification of the crude product gave the desired product as an oil; yield 7.42 g. (58.3%). IR absorption spectrum (liquid film): 3430, 2930, 2855, 2700 –2400, 1735, 1710, 1440, 1380, 1245, 1200, 1125, 1080, 1025 cm$^{-1}$; NMR spectrum (in CDCL$_3$, TMS as internal standard): δ: 0.7 – 1.05 (9H, multiplet), 1.05 – 2.65 (34H, multiplet), 3.3 – 4.3 (7H, multiplet), 4.4 – 4.7 (2H, multiplet), 4.7 – 5.2 (2H, broad peak), 5.3 – 5.65 (2H, multiplet)$_{ppm}$.

EXAMPLE 14

Preparation of 9α-hydroxy-11α,15$\xi$-ditetrahydropyranyloxy-15($\xi$),16(R)-dimethyl-prost-cis-5-enoic acid To a solution of 2.19 g. of 4-carboxy-n- butyltriphenylphosphonium bromide in dimethylsulphoxide was added dropwise a solution of sodiomethylsulphinylcarbanide prepared by the method described in Example 4 from 4.06 g. of sodium hydride (55% content) and dimethylsulphoxide. A solution of 9.3 g. of 2-oxa-3-hydroxy-6-syn-(3$\xi$-tetrahydropyranyloxy-3($\xi$),4(R)-dimethyl-octyl)-7-anti-tetrahydropyranyloxy-cis-bicyclo[3,3,0 octane [cf. Reference Example 29] in dimethylsulphoxide was added, and stirring continued at room temperature for 2 hours to complete the reaction. Usual working-up of the reaction mixture and purification by column chromatography of the crude product gave the desired product as an oil; yield 5.43 g. (49.2%). IR absorption spectrum (liquid film): 3400, 2940, 2860, 2700 – 2400, 1740, 1710, 1440, 1380, 1240, 1205, 1130, 1080, 1030 cm$^{-1}$; NMR spectrum (in CDCL$_3$, TMS as internal standard); δ: 0.75 – 1.05 (6H, multiplet), 1.05 – 2.65 (38H, multiplet), 3.4 – 4.3 (6 H, multiplet), 5.2 – 5.7 (4H, broad peak and multiplet)$_{ppm}$.

EXAMPLE 15

Preparation of 2α-(6-carboxy-hex-cis-2-enyl)-3β-(3ξ-tetrahydropyranyloxy-4(ξ)-phenyl-pentyl)-4α-tetrahydropyranyloxy-cyclopentan-1α-ol 6.25 g. of sodium hydride (55% content) was added to 75 ml. of dimethylsulphoxide and the mixture heated at 70°C. until the evolution of hydrogen ceased. After cooling, the resulting solution of sodiomethylsulphinylcarbanide was added to a solution of 33.6 g. of 4-carboxy-n-butyl-triphenylphosphonium bromide in 67 ml. of dimethylsulphoxide at room temperature. Five minutes later, a solution of 14.4 g. of 2-oxa-3-hydroxy-6-syn-(3ξ-tetrahydropyranyloxy-4(ξ)-phenyl-pentyl)-7-anti-tetrahydropyranyloxy-cis-bicyclo[3,3,0]octane [prepared as described in Reference Example 28] in 55 ml. of dimethylsulphoxide was added, and the reaction mixture stirred at about 25°C. for 2.5 hours. After completion of the reaction, the reaction mixture was worked-up and the product purified following the procedure described in Example 4 to give the desired product as an oil; yield 9.5 g. (56.0%). IR absorption spectrum (liquid film): 3450, 3060, 2940, 2700 – 1300, 1740, 1710, 1600, 1450, 1380, 1245, 1205, 1135, 1080, 1025 cm$^{-1}$; NMR spectrum (in CDCl$_3$, TMS as internal standard): δ: 1.0 – 3.0 (32H, multiplet), 3.4 – 4.3 (7H, multiplet), 4.3 – 4.7 (2H, multiplet), 5.0 – 5.65 (4H, broad peak and multiplet), 7.1 – 7.4 (5H, multiplet)$_{ppm}$.

EXAMPLE 16

Preparation of 2α-(6-carboxy-hex-cis-2-enyl)-3β-(3α-tetrahydropyranyloxy-4(ξ)-cyclohexyl-pentyl)-4α-tetrahydropyranyloxy-cyclopentan-1α-ol A solution of sodiomethylsulphinylcarbanide was prepared in the same manner as described in Example 13 from 7.30 g. of sodium hydride (55% content) and 95 ml. of dimethylsulphoxide. The resulting solution was added to a solution of 39.4 g. of 4-carboxy-n-butyl-triphenylphosphonium bromide in 80 ml. of dimethylsulphoxide at room temperature. A solution of 17.1 g. of 2-oxa-3-hydroxy-6-syn-(3α-tetrahydropyranyloxy-4(ξ)-cyclohexylpentyl)-7-anti-tetrahydropyranyloxy-cis-bicyclo[3,3,0]-octane [cf. Reference Example 29] dissolved in 65 ml. of dimethylsulphoxide was then added with stirring, and the mixture allowed to react for 2.5 hours. Working-up of the reaction mixture and purification of the product in the usual way gave the desired product as a colourless oil; yield 10.6 g. (52.8%). IR absorption spectrum (liquid film): 3440, 2940, 2700 – 2400, 1740, 1710, 1450, 1380, 1240, 1205, 1135, 1080, 1025 cm$^{-1}$; NMR spectrum (in CDCL$_3$, TMS as internal standard): δ: 0.55 – 1.0 (3H, multiplet), 1.05 – 2.65 (4OH, multiplet), 3.3 – 4.3 (7H, multiplet), 4.3 – 4.8 (4H, broad peak and multiplet), 5.25 – 5.65 (2H, multiplet)$_{ppm}$.

EXAMPLE 17

Preparation of 2α-(6-carboxy-hex-cis-2-enyl)-3β-(3α-tetrahydropyranyloxy-4(ξ)-cyclopentyl-butyl)-4α-tetrahydropyranyloxy-cyclopentan-1α-ol A solution of sodiomethylsulphinylcarbanide was prepared according to the method described in Example 15 from 7.05 g. of sodium hydride (55% content) and 80 ml. of dimethylsulphoxide. The reagent thus prepared was added at about 25°C. to a solution of 37.4 g. of 4-carboxy-n-butyl-triphenylphosphonium bromide in 72 ml. of dimethylsulphoxide. Subsequently a solution of 15.3 g. of 2-oxa-3-hydroxy-6-syn-3α-tetrahydropyranyloxy-4(ξ)-cyclopentyl-butyl)-7-anti-tetrahydropyranyloxy-cis-bicyclo[3,3,0]octane [prepared as described in Reference Example 29] in 58 ml. of dimethylsulphoxide was added, and the reaction mixture stirred for 2 hours at room temperature. After completion of the reaction, the reaction mixture was worked-up and the product purified in the usual way to give the desired product as an oil; yield 9.3 g. (51.1%). IR absorption spectrum (liquid film): 3420, 2945, 2865, 2700 –2300, 1740, 1710, 1440, 1380, 1245, 1205, 1135, 1080, 1025 cm$^{-1}$; NMR spectrum (in CDCl$_3$, TMS as internal standard): δ: 1.05 – 2.7 (39H, multiplet), 3.3 – 4.3 (7H, multiplet), 4.4 – 4.7 (2H, multiplet), 4.9 – 5.65 (4H, broad peak and multiplet)$_{ppm}$.

EXAMPLE 18

Preparation of 2α-(6-carboxy-hex-cis-2-enyl)-3β-(3ξ-tetrahydropyranyloxy-4-(ξ)-cyclopentyl-pentyl)-4α-tetrahydropyranyloxy-cyclopentan-1α-ol A solution of sodiomethylsulphinylcarbanide was prepared according to the method described in Example 15 from 3.10 g. of sodium hydride (55% content) and 30 ml. of dimethylsulphoxide. The reagent thus prepared was added at about 25°C. to a solution of 16.2 g. of 4-carboxy-n-butyl-triphenylphosphonium bromide in 50 ml. of dimethylsulphoxide, 6.77 g. of 2-oxa-3-hydroxy-6-syn-(3ξ-tetrahydropyranyloxy-4(ξ)-cyclopentyl-pentyl)-7-anti-tetrahydropyranyl-oxy-cis-bicyclo[3,3,0]octane [prepared as described in Reference Example 30] in 50 ml. of dimethylsulphoxide was added, and the reaction mixture stirred for 2 hours at room temperature. After completion of the reaction, the reaction mixture was worked up and the product purified in the usual way to give 3.63 g. (45.6%) of the pure desired product. IR absorption spectrum (liquid film): 3450, 2940, 2860, 2750~2400, 1730, 1120, 1080, 1035, 1025 cm$^{-1}$; NMR spectrum (in CDCl$_3$, TMS as internal standard): δ: 0.73~1.10 (3H, doublet), 4.63~5.00 (2H, multiplet), 5.35~5.80 (2H, multiplet), 6.15~6.80 (2H, broad singlet).

EXAMPLE 19

Preparation of 13,14-dihydro-ω-bis-homo-prostaglandin-F$_{2α}$ 3.15 g. of 9α-hydroxy-11α,15α-ditetrahydropyranyloxy-ω-bis-homo-prost-cis-5-enoic acid [prepared as described in Example 4] were dissolved in 95 ml. of a mixture of acetic acid, water and tetrahydrofuran (20:10:3), and the reaction mixture was stirred at 38°–43°C. for 2 hours. It was then poured into about 500 ml. of chilled water, and extracted with ethyl acetate. The ethyl acetate layer was washed with water, dried over magnesium sulphate and evaporated in vacuo to remove the solvent. The residue was subjected to column chromatography using 100 g. of silica gel and ethyl acetate-cyclohexane (3:1) as eluent to give 1.47 g. (67.1%) of the desired product as a colourless oil. IR absorption spectrum (liquid film); 3380, 2940, 2855, 2700 – 2350, 1705, 1410, 1240 cm$^{-1}$; NMR spectrum (in CDCl$_3$, TMS as internal standard): δ: 0.91 (3H, triplet)$_{ppm}$, 1.05 – 2.65 (28H, multiplet)$_{ppm}$, 3.50 – 4.26 (3H, multiplet)$_{ppm}$, 4.3 – 4.7 (4H, broad peak)$_{ppm}$, 5.25 – 5.60 (2H, multiplet)$_{ppm}$;

Elementary analysis: Calculated for C$_{22}$H$_{40}$O$_5$ C, 68.71, H 10.49% Found C, 68.49, H 10.63%.

EXAMPLE 20

Preparation of
13,14-dihydro-ω-nor-prostaglandin-F$_{2\alpha}$ 2.23 g. of 9α-hydroxy-11α,15α-ditetrahydropyranyloxy-ω-norprost-cis-5-enoic acid [prepared as described in Example 5] were dissolved in 60 ml. of a mixture of acetic acid, water and tetrahydrofuran (20:10:3) and the reaction mixture was stirred at 40° – 45°C. for 1.5 hours. The reaction mixture was then poured into chilled water, and extracted with ethyl acetate. Concentration, followed by silica gel column chromatography using ethyl acetatecyclohexane (3:1) as eluent, gave 916 mg. (61.3%) of the desired product as a colourless oil. IR absorption spectrum (liquid film): 3360, 2920, 2850, 2700 – 2300, 1710, 1410, 1240 cm$^{-1}$; NMR spectrum (in CDCl$_3$, TMS as internal standard): δ: 0.90 (3H, triplet)$_{ppm}$, 1.05 – 2.65 (22H, multiplet)$_{ppm}$, 3.48 – 4.25 (3H, multiplet)$_{ppm}$, 4.5 – 5.0 (4H, broad peak), 5.25 – 4.60 (2H, multiplet)$_{ppm}$;

Elementary analysis: Calculated at C$_{19}$H$_{34}$O$_5$ C, 66.63, H, 10.01% Found C, 66.81, H, 10.28%.

EXAMPLE 21

Preparation of
13,14-dihydro-16(R)-methyl-prostaglandin-F$_{2\alpha}$

Following the procedure of Example 19, 2.85 g. of 9α-hydroxy-11α,15α-ditetrahydropyranyloxy-16(R)-methylprost-cis-5-enoic acid [prepared as described in Example 6] were treated, the reaction mixture worked-up, and the crude product purified by subjecting it to column chromatography to give 1.22 g. (62.2%) of the desired product as a colourless oil. IR absorption spectrum (liquid film): 3350, 2925, 2850, 2700 – 2350, 1710, 1410, 1240 cm$^{-1}$; NMR spectrum (in CDCl$_3$, TMS as internal standard): δ: 0.75 – 1.05 (6H, multiplet)$_{ppm}$, 1.05 – 2.65 (23H, multiplet)$_{ppm}$, 3.50 – 4.28 (3H, multiplet)$_{ppm}$, 4.4 – 4.9 (4H, broad peak), 5.25 – 5.60 (2H, multiplet);

Elementary analysis: Calculated for C$_{21}$H$_{38}$O$_5$ C, 68.07, H, 10.34% Found C, 67.88, H 10.51%.

EXAMPLE 22

Preparation of
13,14-dihydro-16,16-dimethyl-prostaglandin-F$_{2\alpha}$

The desired product, 897 mg. (68.7%), as an oil was obtained from 1.88 g. of 9α-hydroxy-11α-15α-ditetrahydropyranyloxy-16,16-dimethyl-prost-cis-5-enoic acid [prepared as described in Example 7] following the procedure of Example 19 with the same reaction conditions, working up and column chromatography.

IR absorption spectrum (liquid film): 3370, 2930, 2855, 2700 – 2400, 1710, 1450, 1245 cm$^{-1}$; NMR spectrum (in CDCl$_3$, TMS as internal standard): δ: 0.75 – 1.05 (9H, multiplet)$_{ppm}$, 1.05 – 2.6 (22H, multiplet)$_{ppm}$, 3.50 – 4.30 (3H, multiplet)$_{ppm}$, 4.3 – 4.8 (4H, broad peak), 5.25 – 5.58 (2H, multiplet)$_{ppm}$;

Elementary analysis: Calculated for C$_{22}$H$_{40}$O$_5$ C, 68.71 H, 10.49% Found C, 68.94 H, 10.72%.

EXAMPLE 23

Preparation of
13,14-dihydro-17(ξ)-methylprostaglandin-F$_{2\alpha}$ 2.07 g. of 9α-hydroxy-11α,15α-ditetrahydropyranyloxy-17(ξ)-methyl-prost-cis-5-enoic acid [prepared as described in Example 9] were dissolved in a mixture of 41 ml. of 0.7N hydrochloric acid and 41 ml. of tetrahydrofuran, and the reaction mixture was stirred at 25° – 30°C. for 2 hours. It was then poured into 250 ml. of chilled water and extracted with ethyl acetate. The extract was washed with water, dried, concentrated, and the residue subjected to column chromatography using 80 g. of silica gel and ethyl acetate-cyclohexane (3:1) as eluent to give 881 mg. (61.8%) of the desired product as a colourless oil. IR absorption spectrum (liquid film): 3380, 2940, 2855, 2700 – 2400, 1710 – 1440, 1380, 1245 cm$^{-1}$; NMR spectrum (in CDCl$_3$, TMS as internal standard): δ: 0.75–1.02 (6H, multiplet)$_{ppm}$, 1.05–2.65 (23H, multiplet)$_{ppm}$, 3.48–4.28 (3H, multiplet), 4.9–5.65 (6H, broak peak & multiplet)$_{ppm}$;

Elementary analysis: Calculated for C$_{21}$H$_{38}$O$_5$ C, 68.07 H, 10.34% Found C, 68.31 H, 10.23%.

EXAMPLE 24

Preparation of
13,14-dihydro-19(ξ)-methyl-prostaglandin-F$_{2\alpha}$

From 1.46 g. of 9α-hydroxy-11α,15α-ditetrahydropyranyloxy-19(ξ)-methyl-prost-cis-5-enoic acid [prepared as described in Example 11] 674 mg. (67.0%) of the desired product was obtained as a colourless oil by the procedure described in Example 19. IR absorption spectrum (liquid film): 3380, 2935, 2850, 2700 – 2350, 1710, 1410, 1245 cm$^{-1}$; NMR spectrum (in CDCl$_3$, TMS as internal standard): δ: 0.89 (6H, doublet)$_{ppm}$, 1.05 – 2.65 (23H, multiplet), 3.50 – 4.30 (3H, multiplet)$_{ppm}$, 4.7 – 5.2 (4H, broad peak)$_{ppm}$ 5.25 – 5.60 (2H, multiplet)$_{ppm}$;

Elementary analysis: Calculated for C$_{21}$H$_{38}$O$_5$ C, 68.07, H, 10.34% Found C, 67.93, H, 10.27%.

EXAMPLE 25

Preparation of
13,14-dihydro-15(ξ)-methyl-prostaglandin-F$_{2\alpha}$ 1.49 g. of 9α-hydroxy-11α,15ξ-ditetrahydropyranyloxy-15(ξ)-methyl-prost-cis-5-enoic acid [prepared as described in Example 12] were treated and the reaction mixture worked-up in the same manner as described in Example 23. The resulting crude product was purified by subjecting it to silica gel column chromatography and eluting with ethyl acetate-cyclohexane (3:1). 577 mg. (52.2%) of the desired product was obtained as a colourless oil. IR absorption spectrum (liquid film): 3370, 2930, 2850, 2700 – 2300, 1705, 1440, 1380, 1240 cm$^{-1}$; NMR spectrum (in CDCl$_3$, TMS as internal standard): δ: 0.88 (3H, triplet)$_{ppm}$, 1.05 – 2.6 (27H, multiplet)$_{ppm}$, 3.75 – 4.25

(2H, multiplet)$_{ppm}$, 4.6 – 5.1 (4H, broad peak)$_{ppm}$, 5.25 – 5.60 (2H, multiplet)$_{ppm}$;

Elementary analysis: Calculated for $C_{21}H_{38}O_5$ C, 68.07, H, 10.34% Found C, 68.25 H, 10.39%.

EXAMPLE 26

Preparation of 3($\xi$)-dimethyl-13,14-dihydroprostaglandin-$F_{2\alpha}$

From 1.79 g. of 3($\xi$),16($\xi$)-dimethyl-9$\alpha$-hydroxy-11$\alpha$,15$\alpha$-ditetrahydropyranyloxy-prost-cis-5-enoic acid [prepared as described in Example 13] there was obtained 776 mg. (62.5%) of the desired product as a colourless oil with the same reaction conditions, working-up procedure and purification of the product as described in Example 23. IR absorption spectrum (liquid film): 3370, 2940, 2860, 2700 – 2350, 1710, 1380, 1245 cm$^{-1}$; NMR spectrum (in CDCl$_3$, TMS as internal standard): $\delta$: 0.7 – 1.05 (9H, multiplet)$_{ppm}$, 1.05 – 2.7 (22H, multiplet)$_{ppm}$, 3.5 – 4.30 (3H, multiplet)$_{ppm}$, 4.4 – 5.1 (4H, broad peak)$_{ppm}$, 5.28 – 5.65 (2H, multiplet)$_{ppm}$;

Elementary analysis: Calculated for $C_{22}H_{40}O_5$ C, 68.71 H, 10.49%. Found C, 68.84 H, 10.32%.

EXAMPLE 27

Preparation of 13,14-dihydro-15($\xi$),16(R)-dimethylprostaglandin-$F_{2\alpha}$ 1.03 g. of 9$\alpha$-hydroxy-11$\alpha$,15$\xi$-ditetrahydropyranyloxy-15($\xi$),16(R)-dimethyl-prost-cis-5-enoic acid [prepared as described in Example 14] were treated, the reaction mixture worked-up and the product purified by column chromatography according to the procedure described in Example 23. The desired product was obtained as a colourless oil in a yield of 452 mg. (63.1%). IR absorption spectrum (liquid film): 3380, 2945, 2860, 2700 – 2300, 1710, 1440, 1410, 1245 cm$^{-1}$; NMR spectrum (in CDCl$_3$, TMS as internal standard): $\delta$: 0.75 – 1.05 (6H, multiplet)$_{ppm}$, 1.05 – 2.65 (26H, multiplet)$_{ppm}$, 3.70 – 4.30 (2H, multiplet)$_{ppm}$; 4.3 – 4.8 (4H, broad peak)$_{ppm}$, 5.25 – 5.60 (2H, multiplet)$_{ppm}$;

Elementary analysis: Calculated for $C_{22}H_{40}O_5$ C, 68.71 H, 10.49%. Found C, 68.55, H, 10.58%.

EXAMPLE 26

Preparation of 2$\alpha$-(6-carboxy-hex-cis-2-enyl)-3$\beta$-(3$\xi$-hydroxy-4($\xi$)-phenyl-pentyl)-4$\alpha$-hydroxy-cyclopentan-1$\alpha$-ol [or 16($\xi$)-phenyl-$\omega$-trinor-13,14-dihydroprostaglandin-$F_{2\alpha}$ ]

2.44 g. of the product of Example 15 were dissolved in 70 ml. of a mixture of acetic acid, water and tetrahydrofuran (20:10:3), and the reaction mixture was stirred at 40°– 45°C. for 1.5 hours. It was then poured into about 350 ml. of chilled water and extracted with ethyl acetate. Washing with water, drying, concentration in vacuo, and finally silica gel column chromatography of the product with ethyl acetatecyclohexane as eluent gave 1.17 g. (68.6%) of the desired product as an oil. IR absorption spectrum (liquid film): 3350, 3030, 2920, 2700 – 2300, 1705, 1600, 1490, 1445, 1240 cm$^{-1}$; NMR spectrum (in CDCl$_3$, TMS as internal standard): $\delta$: 1.0 – 3.0 (20H, multiplet)$_{ppm}$, 3.45 – 4.25 (3H, multiplet)$_{ppm}$, 4.8 – 5.7 (6H, broad peak & multiplet)$_{ppm}$, 7.0 – 7.5 (5H, multiplet);

Elementary analysis: Calculated for $C_{23}H_{34}O_5$ C, 70.74 H, 8.78%. Found C, 70.61, H, 8.86%.

EXAMPLE 29

Preparation of 2$\alpha$-(6-carboxy-hex-cis-2-enyl)-3$\beta$-(3$\alpha$-hydroxy-4($\xi$)-cyclohexyl-pentyl)-4$\alpha$-hydroxy-cyclopentan-1$\alpha$-ol [or 16($\xi$)-cyclohexyl-$\omega$-trinor-13,14-dihydroprostaglandin-$F_{2\alpha}$ ]

From 2.09 g. of the product of Example 16 934 mg. (63.7%) of the desired product were obtained as a colourless oil using the same reaction conditions, working-up of the reaction mixture and purification of the product as described in Example 28. IR absorption spectrum (liquid film): 3360, 2930, 2700 – 2300, 1710, 1440, 1380, 1240 cm$^{-1}$; NMR spectrum (in CDCl$_3$, TMS as internal standard): $\delta$: 0.55 – 1.05 (3H, multiplet)$_{ppm}$, 1.05 – 2.7 (28H, multiplet)$_{ppm}$, 3.50 – 4.30 (3H, multiplet)$_{ppm}$, 4.6 – 5.2 (4H, broad peak)$_{ppm}$, 5.25 – 5.60 (2H, multiplet)$_{ppm}$;

Elementary analysis: Calculated for $C_{23}H_{40}O_5$ C, 69.66 H, 10.17%. Found C, 69.43 H, 10.36%.

EXAMPLE 30

Preparation of 2$\alpha$-(6-carboxy-hex-cis-2-enyl)-3$\beta$-(3$\alpha$-hydroxy-4($\xi$)-cyclopentyl-butyl)-4$\alpha$-hydroxy-cyclopentan-1$\alpha$-ol [or 16($\xi$)-cyclopentyl-$\omega$-tetranor-13,14-dihydroprostaglandin-$F_{2\alpha}$ ]

2.16 g. of the product of Example 17 were treated, the reaction mixture worked-up and the product subjected to chromatographic purification as described in Example 28 to yield 996 mg. (67.1%) of the desired product as a colourless oil. IR absorption spectrum (liquid film): 3380, 2925, 2700 – 2300, 1710, 1410, 1380, 1240 cm$^{-1}$; NMR spectrum (in CDCl$_3$, TMS as internal standard); $\delta$: 1.0 – 2.65 (27H, multiplet)$_{ppm}$, 3.50 – 4.30 (2H, multiplet)$_{ppm}$, 4.4 – 4.9 (4H, broad peak)$_{ppm}$, 5.25 – 5.60 (2H, multiplet)$_{ppm}$;

Elementary analysis: Calculated for $C_{21}H_{36}O_5$ C, 68.44 H, 9.85%. Found C, 68.21 H, 9.73%.

EXAMPLE 31

Preparation of 13,14-dihydro-$\omega$-bis homo-prostaglandin-$E_2$

To a solution of 6.28 g of the product of Example 4 in 200 ml of diethyl ether at 0°C. a chromic acid solution (chromic trioxide 7.9 g, manganese sulphate 38.6 g., conc. sulphuric acid 8.9 ml, in water 190 ml) was added and the reaction mixture stirred vigorously for 2 hours at 0°– 5°C. A further 200 ml. of diethyl ether was added to the reaction mixture, and the organic layer was separated. The aqueous layer was extracted three times with diethyl ether and the combined organic layers were washed thoroughly with water until no more colouration of the washings was observed. After drying over magnesium sulphate the diethyl ether was removed by distillation in vacuo, and the resulting crude product, i.e. 9-oxo-11$\alpha$, 15$\alpha$-ditetrahydropyranyloxy-$\omega$-bis-homo-prost-cis-5-enoic acid, was dissolved in 125 ml of a mixture of acetic acid, water and tetrahydrofuran (20:10:3) and the reaction mixture stirred at 40°C for 3 hours. It was then poured into about 600 ml of chilled water and extracted with ethyl acetate. Drying, evaporation of the solvent in vacuo followed by column chromatographic purification of the product using 180 g. of silica gel and ethyl acetate-cyclohexane (1:1) as eluent gave 2.33 g. (53.7%) of the desired product as a colourless oil. IR absorption spectrum (liquid film): 3400, 2925, 2855, 2700 – 2300, 1740, 1710, 1245, 1160, 1055 cm$^{-1}$; NMR spectrum (in CDCl$_3$, TMS as internal standard): δ: 0.90 (3H, triplet)$_{ppm}$, 1.05 – 2.95 (28H, multiplet)$_{ppm}$, 3.50 – 3.85 (1H, multiplet)$_{ppm}$, 3.9 – 4.4 (4H, broad peak and multiplet)$_{ppm}$, 5.25 – 5.60 (2H, multiplet)$_{ppm}$;

Elementary analysis: Calculated for C$_{22}$H$_{38}$O$_5$ C, 69.07 H, 10.01%. Found C, 68,89 H, 10.26%.

EXAMPLE 32

Preparation of 13,14-dihydro-ω-nor-prostaglandin-E$_2$ 5.30 g. of the product of Example 5 were dissolved in 180 ml. of diethyl ether, and a chromic acid solution (chromic trioxide 7.6 g., manganese sulphate 37.2 g., conc. sulphuric acid 8.6 ml., and water 180 ml.) was added at 0°C, and the reaction mixture stirred at 0°–5°C for 3 hours. Diethyl ether was then added and the organic layer separated. The aqueous layer was extracted again with diethyl ether, and the combined ether layers were washed with water, dried, and concentrated in vacuo to produce crude 9-oxo-11α, 15α-ditetrahydropyranyloxy-ω-nor-prost-cis-5-enoic acid. The resulting mass was dissolved in 105 ml. of a mixture of acetic acid, water and tetrahydrofuran (20:10:3) and stirred at 38° – 42°C for 2.5 hours. The reaction mixture was then poured into 500 ml. of water and extracted with ethyl acetate. Washing of the ethyl acetate layer, drying and concentration in vacuo, followed by silica gel column chromatography [ silica gel 160 g., eluent:ethyl acetate-cyclohexane (1:1)] gave 1.78 g. (50.5%) of the desired product as a colourless oil. IR absorption spectrum (liquid film): 3400, 2930, 2700 – 2300, 1740, 1710, 1455, 1380, 1245, 1160, 1080, 1055 cm$^{-1}$; NMR spectrum (in CDCl$_3$, TMS as internal standard): δ: 0.89 (3H, triplet)$_{ppm}$, 1.05 – 2.9 (22H, multiplet)$_{ppm}$, 3.50 – 3.85 (1H, multiplet)$_{ppm}$, 4.0 – 4.5 (4H, broad peak and multiplet)$_{ppm}$, 5.28 – 5.60 (2H, multiplet)$_{ppm}$;

Elementary analysis: Calculated for C$_{19}$H$_{32}$O$_5$ C, 67.03 H, 9.47%. Found C, 67.21 H, 9.65%.

EXAMPLE 33

Preparation of 13,14-dihydro-16(R)-methyl-prostaglandin-E$_2$

From 7.33 g of the product of Example 6 there were obtained 2.42 g. (48.3%) of the title product in the form of a colourless oil, following the procedure of Example 31. IR absorption spectrum (liquid film); 3400, 2920, 2700 – 2300, 1735, 1705, 1450, 1240, 1165, 1075 cm$^{-1}$; NMR spectrum (in CDCl$_3$, TMS as internal standard); δ: 0.75 – 1.05 (6H, multiplet)$_{ppm}$, 1.05 – 2.95 (23H, multiplet)$_{ppm}$, 3.50 – 3.85 (1H, multiplet), 4.0 – 4.35 (1H, multiplet)$_{ppm}$, 4.4 – 4.9 (3H, broad peak), 5.25 - 5.55 (2H, multiplet)$_{ppm}$;

Elementary analysis: Calculated for C$_{21}$H$_{36}$O$_5$ C, 68.44 H, 9.85%. Found C, 68.61 H, 9.72%

EXAMPLE 34

Preparation of 13,14-dihydro-16,16-dimethyl-prostaglandin-E$_2$ 4.47 g. of the product of Example 7 were dissolved in 140 ml. of diethyl ether and a chromic acid solution (chromic trioxide 5.5 g., manganese sulphate 27.0 g., conc. sulphuric acid 6.2 ml., and water 133 ml.) was added at 0°C, and the reaction mixture stirred with ice-cooling for 3 hours. More diethyl ether was added to the reaction mixture as in Example 31, the organic layer was separated and washed successively with water and 50% saturated aqueous sodium chloride, and then dried and concentrated in vacuo. The residue on evaporation, i.e. 9-oxo-11α,15α-ditetrahydropyranyloxy-16,16-dimethylprost-cis-5-enoic acid, was dissolved in 85 ml. of a mixture of acetic acid, water and tetrahydrofuran (20:10:3), the solution stirred at about 40°C for 2.5 hours, poured into chilled water, and extracted with ethyl acetate. Washing with water, drying, concentration and purification of the product by silica gel column chromatography gave 1.43 g. (46.5%) of the title compound as an oil. IR absorption spectrum (liquid film): 3380, 2925, 2855, 1740, 1710, 1240, 1160 cm$^{-1}$; NMR spectrum (in CDCl$_3$, TMS as internal standard): δ: 0.75 – 1.05 (9H, multiplet)$_{ppm}$, 1.05 – 2.95 (22 H, multiplet)$_{ppm}$, 3.50 – 3.85 (1H, multiplet)$_{ppm}$, 4.0 – 4.5 (4H, broad peak and multiplet)$_{ppm}$, 5.25–5.58 (2H, multiplet)$_{ppm}$;

Elementary analysis: Calculated for C$_{22}$H$_{38}$O$_5$ C, 69.07 H, 10.01%. Found C, 69.26 H, 10.22%.

EXAMPLE 35

Preparation of 13,14-dihydro-16(ξ)-ethyl-prostaglandin-E$_2$

From 3.71 g. of the product of Example 8 by the procedure described in Example 31, there were obtained 1.29 g. (50.3%) of the title compound as a colourless oil. IR absorption spectrum (liquid film): 3400, 2930, 2855, 2700 – 2350, 1735, 1705, 1455, 1240 cm$^{-1}$; NMR spectrum (in CDCl$_3$, TMS as internal standard): δ: 0.90 – 1.05 (6H, multiplet)$_{ppm}$, 1.05 – 2.95 (25H, multiplet)$_{ppm}$, 3.50 – 3.80 (1H, multiplet)$_{ppm}$, 4.0 – 4.35 1H, multiplet)$_{ppm}$, 4.4 – 5.0 (3H, broad peak)$_{ppm}$, 5.25 – 5.60 (2H, multiplet)$_{ppm}$;

Elementary analysis: Calculated for C$_{22}$H$_{38}$O$_5$ C, 69.07 H, 10.01%. Found C, 69.21 H, 9.88%.

EXAMPLE 36

Preparation of 13,14-dihydro-17(ξ)-methyl-prostaglandin-E$_2$

From 4.68 g. of the product of Example 9, the title compound was obtained as a colourless oil in a yield of 1.44 g. (45.0%), following the procedure described in Example 31. IR absorption spectrum (liquid film): 3380, 2925, 2850, 2700–2300, 1740, 1710, 1380, 1240 cm$^{-1}$; NMR spectrum (in CDCl$_3$, TMS as internal standard): δ: 0.75 – 1.05 (6H, multiplet)$_{ppm}$, 1.05 – 2.9 (23H, multiplet)$_{ppm}$, 3.50 – 3.82 (1H, multiplet)$_{ppm}$, 4.0 – 4.32 (1H, multiplet)$_{ppm}$, 4.5 – 5.2 (3H, broad peak)$_{ppm}$, 5.28 – 5.58 (2H, multiplet)$_{ppm}$;

Elementary analysis: Calculated for C$_{21}$H$_{36}$O$_5$ C, 68.44 H, 9.85% Found C, 68.59 H, 10.06%.

EXAMPLE 37

Preparation of 13,14-dihydro-15(ξ)-methyl-prostaglandin-E$_2$.

From 3.64 g. of the product of Example 12, following the procedure described in Example 31 and purification of the product by column chromatography, 1.28 g. (51.4%) of the title compound was obtained as a colourless oil. IR absorption spectrum (liquid film): 3400, 2930, 2855, 2700 – 2300, 1740, 1710, 1380, 1240, 1160 cm$^{-1}$; NMR spectrum (in CDCl$_3$, TMS as internal standard): δ: 0.88 (3H, triplet)$_{ppm}$, 1.05 – 2.95 (27H, multiplet)$_{ppm}$, 3.9 – 4.5 (4H, broad peak and multiplet)$_{ppm}$, 5.25 – 5.55 (2H, multiplet)$_{ppm}$;

Elementary analysis: Calculated for C$_{21}$H$_{36}$O$_5$ C, 68.44 H, 9.85%. Found C, 68.58 H, 9.99%

EXAMPLE 38

Preparation of 3(ξ)16(ξ)-dimethyl-13,14-dihydro-prostaglandin-E$_2$ 3.13 g. of the product of Example 13 were dissolved in 100 ml. of diethyl ether and a chromic acid solution (chromic trioxide 3.4 g., manganese sulphate 19.4 g., conc. sulphuric acid 4.4 ml., and water 95 ml.) was added at 0°C., and the reaction mixture was stirred vigorously at 0° – 3°C for 3 hours. The crude product obtained by extraction with diethyl ether, i.e. 3(ξ),16(ξ)-dimethyl-9-oxo-11α,15α-ditetrahydropyranyloxy-prost-cis-5enoic acid, was then dissolved in 60 ml. of a mixture of acetic acid, water and tetrahydrofuran (20:10:3) and the reaction mixture stirred at 40° – 45°C for 2 hours. After completion of the reaction, the reaction mixture was poured into chilled water, extracted with ethyl acetate and the crude product subjected to silica gel column chromatography [eluent, cyclohexane-ethyl acetate (1:1) to give 1.006 g. (46.4%) of the title compound as an oil. IR absorption spectrum (liquid film): 3370, 2925, 2850, 2700 – 2300, 1740, 1710, 1455, 1240 cm$^{-1}$; NMR spectrum (in CDCl$_3$, TMS as internal standard): δ: 0.75 – 1.05 (9H, multiplet)$_{ppm}$, 1.05 – 2.95 (22H, multiplet)$_{ppm}$, 3.50 – 3.85 (1H, multiplet$_{ppm}$, 3.95 – 4.25 (1H, multiplet)$_{ppm}$, 5.1 – 5.6 (5H, broad peak and multiplet)$_{ppm}$;

Elementary analysis: Calculated for C$_{22}$H$_{38}$O$_5$ C, 69.07 H, 10.01%. Found C, 69.24 H, 10.18%

EXAMPLE 39

Preparation of 13,14-dihydro-15(ξ),16(R)-dimethyl-prostaglandin-E$_2$

Starting from 2.98 g. of the product of Example 14, 1.07 g. (50.6%) of the desired product was obtained as a colourless oil, following the procedure described in Example 31. IR absorption spectrum (liquid film): 3400, 2920, 2700 – 2300, 1740, 1710, 1380, 1245, 1160 cm$^{-1}$; NMR spectrum (in CDCl$_3$, TMS as internal standard): δ: 0.75 – 1.05 (6H, multiplet)$_{ppm}$, 1.05 – 2.95 (26H, multiplet)$_{ppm}$, 3.9 – 4.6 (4H, broad peak and multiplet)$_{ppm}$, 5.25 – 5.55 (2H, multiplet)$_{ppm}$;

Elementary analysis: Calculated for C$_{22}$H$_{38}$O$_5$ C, 69.07 H, 10.01% Found C, 68.94 H, 10.27%.

EXAMPLE 40

Preparation of 2α-(6-carboxy-hex-cis-2enyl)-3β-(3ξ-hydroxy-4(ξ)-phenyl-pentyl)-4α-hydroxy-cyclopentanone [or 16(ξ)-phenyl-ω-trinor-13,14-dihydroprostaglandin-E$_2$]

To a cold solution of 4.45 g. of the product of Example 15 in 140 ml. of diethyl ether was added a chromic acid solution (chromic trioxide 5.5 g., manganese sulphate 27.0 g., conc. sulphuric acid 6.2 ml., and water 135 ml.) and the reaction mixture was stirred vigorously at 0°–3°C for 2.5 hours.

The ether layer was separated after completion of the reaction and the aqueous layer extracted with diethyl ether. The combined ether solutions were washed thoroughly with water, dried and evaporated in vacuo. The crude product thus obtained, i.e. 2α-(6-carboxy-hex-cis-2-enyl)-3β-(3ξ-tetrahydropyranyloxy)-4(ξ)-phenyl-pentyl)-4α-tetrahydropyranyloxy-cyclopentanone, was dissolved in 85 ml. of a mixture of acetic acid, water and tetrahydrofuran (20:10:3), and the mixture stirred at about 40°C. for 2 hours. The reaction mixture was then poured into approximately 350 ml. of chilled water, extracted three times with ethyl acetate, and the extracts washed successively with water and 50% saturated aqueous sodium chloride. Drying, evaporation followed by column chromatographic purification of the crude product [silica gel 130 g; eluent, ethyl acetate-cyclohexane (1:1)] gave 1.39 g. (44.9%) of the title compound. IR absorption spectrum (liquid film): 3360, 2920, 2700-2300, 1740, 1710, 1600, 1445, 1240 cm$^{-1}$; NMR spectrum (in CDCl$_3$, TMS as internal standard): δ: 1.0 – 2.95 (20H, multiplet)$_{ppm}$, 3.45 – 3.80 (1H, multiplet)$_{ppm}$, 3.85 – 4.2 (1H, multiplet)$_{ppm}$, 5.20 – 5.55 (2H, multiplet), 5.6 – 6.2 (3H, broad peak)$_{ppm}$, 7.0 – 7.4 (5H);

Elementary analysis: Calculated for C$_{23}$H$_{32}$O$_5$ C, 71.10 H, 8.30%. Found C,70.96 H, 8.37%.

EXAMPLE 41

Preparation of 2α-(6carboxy-hex-cis-2-enyl)-3β-(3ξ-hydroxy-4(ξ)-cyclohexyl-pentyl)-4α-hydroxy-cyclopentanone [or 16 (ξ)-cyclohexyl-ω-trinor-13,14-dihydro-prostaglandin-E$_2$]

Starting from 5.50 g of the product of Example 16, 2.04 g (53.1%) of the title compound was obtained as an oil, following the procedure of Example 40. IR absorption spectrum (liquid film): 3380, 2925, 2700–2300, 1740, 1710, 1380, 1245 cm$^{-1}$;

NMR spectrum (in CDCl$_3$, TMS as internal standard): δ: 0.55 – 1.05 (3H, multiplet)$_{ppm}$, 1.05 – 2.95 (28H, multiplet)$_{ppm}$, 3.50 – 3.85 (1H, multiplet)$_{ppm}$, 4.0 – 4.3 (1H, multiplet)$_{ppm}$, 4.5 – 5.1 (3H, broad peak)$_{ppm}$, 5.28 – 5.60 (2H, multiplet)$_{ppm}$;

Elementary analysis: Calculated for C$_{23}$H$_{38}$O$_5$ C, 70.01 H, 9.71%. Found C, 70.13 H,9.65%

EXAMPLE 42

Preparation of 2α-(6-carboxy-hex-cis-2-enyl)-3β(3α-hydroxy-4-(ξ)-cyclopentyl-butyl)-4α-hydroxy-cyclopentanone [or 16 (ξ)-cyclopentyl-ω-tetranor-13,14, -dihydro-prostaglandin-E$_2$ ]

Following the procedure of Example 40 but starting with 3.84 g. of the product of Example 17, 1.32 g (50.6%) of the title compound was obtained as a colourless oil. IR absorption spectrum (liquid film): 3400, 2930, 2855, 2700 – 2300, 1740, 1710, 1380, 1240, 1160 cm$^{-1}$; NMR spectrum (in CDCl$_3$, TMS as internal standard): δ: 1.05 – 2.95 (27H, multiplet)$_{ppm}$, 3.50 – 3.82 (1H, multiplet)$_{ppm}$, 4.0 – 4.3 (1H, multiplet)$_{ppm}$, 5.1 – 5.6 (5H, broad peak and multiplet)$_{ppm}$;

Elementary analysis: Calculated for C$_{21}$H$_{34}$O$_5$ C, 68.82 H, 9.35%. Found C, 68.67 H, 9.22%.

EXAMPLE 43

Preparation of 13,14-dihydro-ω-nor-prostaglandin-A$_2$ 680 mg. of 13,14-dihydro-ω-nor-prostaglandin E$_2$ [prepared as described in Example 32] were dissolved in 45 ml. of a mixture of tetrahydrofuran and 1N hydrochloric acid (1:1), and the solution stirred at 60°C for 3 hours. The reaction mixture was then poured into chilled water, extracted with ethyl acetate, and the extract washed successively with water and a 50% saturated aqueous sodium chloride solution, dried and concentrated. The residue thus obtained was subjected to column chromatography using 30 g. of silica gel and cyclohexane-ethyl acetate (1:1) as eluent to give 378 mg. (58.7%) of the title compound as an oil. IR absorption spectrum (liquid film): 3400, 2930, 2850, 2700 – 2300, 1740, 1710, 1590, 1450, 1380, 1240 cm$^{-1}$; NMR spectrum (in $CDCl_3$, TMS as internal standard): δ: 0.91 (3H, triplet)$_{ppm}$, 1.05 – 2.9 (26H, multiplet)$_{ppm}$, 3.50 – 3.82 (1H, multiplet)$_{ppm}$, 4.4 – 5.2 (2H, broad peak)$_{ppm}$, 5.30 – 5.60 (2H, multiplet)$_{ppm}$, 6.08 – 6.20 (1H multiplet)$_{ppm}$, 7.54 – 7.68 (1H, multiplet)$_{ppm}$;

Elementary analysis: Calculated for $C_{19}H_{30}O_4$ C, 70.77 H, 9.38%. Found C, 70.89 H, 9.21%.

EXAMPLE 44

Preparation of 13,14-dihydro-16(R)-methyl-prostaglandin-$A_2$

Similar treatment of 753 mg. of 13,14-dihydro-16-(R)-methyl-prostaglandin-$E_2$ [prepared as described in Example 33] by the procedure of Example 43 gave 490 mg. (61.5%) of the title compound as an oil. IR absorption spectrum (liquid film): 3400, 2925, 2700 – 2300, 1740, 1710, 1585, 1455, 1380, 1240 cm$^{-1}$; NMR spectrum (in $CDCl_3$, TMS as internal standard): δ: 0.75 – 1.05 (6H, multiplet)$_{ppm}$, 1.05 – 2.95 (21H, multiplet)$_{ppm}$, 3.50 – 3.82 (1H, multiplet)$_{ppm}$, 4.9 – 5.6 (4H, broad peak and multiplet)$_{ppm}$, 6.06 – 6.18 (1H, multiplet), 7.52 – 7.66 (1H, multiplet);

Elementary analysis: Calculated for $C_{21}H_{34}O_4$ C, 71.96 H, 9.78%. Found C, 71.78 H, 9.55%.

EXAMPLE 45

Preparation of 13,14-dihydro-16,16-dimethyl-prostaglandin-$A_2$ 520 mg. of 13,14-dihydro-16,16-dimethyl-prostaglandin-$E_2$ [prepared as described in Example 34] were dissolved in 50 ml. of a mixture of tetrahydrofuran and 1N hydrochloric acid (1:1) and the solution stirred at 60°C for 3 hours. The reaction mixture was then extracted with ethyl acetate after partial removal of the solvent by concentration in vacuo, washed well with water, dried and concentrated. Column chromatographic purification of the residue as described in Example 43 yielded 278 mg. (56.2%) of the title compound as a colourless oil. IR absorption spectrum (liquid film): 3420, 2930 2700 – 2350, 1740, 1710, 1590, 1450, 1380, 1245 cm$^{-1}$; NMR spectrum (in $CDCl_3$, TMS as internal standard): δ: 0.75 – 1.05 (9H, multiplet)$_{ppm}$, 1.05 – 2.95 (20H, multiplet)$_{ppm}$, 3.50 – 3.80 (1H, multiplet)$_{ppm}$, 4.3 – 4.8 (2H, broad peak)$_{ppm}$, 5.28 – 5.60 (2H, multiplet)$_{ppm}$, 6.08–6.21 (1H, multiplet)$_{ppm}$, 7.54 – 7.68 (1H, multiplet)$_{ppm}$;

Elementary analysis: Calculated for $C_{22}H_{36}O_4$ C, 72.49 H, 9.96%. Found C, 72.65 H, 10.21%.

EXAMPLE 46

Preparation of 13,14-dihydro-15(ξ)-methyl-prostaglandin-$A_2$ 515 mg. of 13,14-dihydro-15(ξ)-methyl-prostaglandin-$E_2$ [prepared as described in Example 37] were subjected to the transformation and working-up procedure described in Example 43 to give 281 mg. (57.4%) of the title compound as a colourless oil. IR absorption spectrum (liquid film): 3400, 2930, 2855, 2700 – 2300, 1740, 1710, 1590, 1455, 1245, 1050 cm$^{-1}$; NMR spectrum (in $CDCl_3$, TMS as internal standard): δ: 0.91 (3H, triplet)$_{ppm}$, 1.05 – 2.9 (25H, multiplet)$_{ppm}$, 4.6 – 5.2 (2H, broad peak)$_{ppm}$, 5.25 – 5.55 (2H, multiplet)$_{ppm}$, 6.10 – 6.22 (1H, multiplet)$_{ppm}$, 7.56 – 7.70 (1H, multiplet)$_{ppm}$;

Elementary analysis: Calculated for $C_{21}H_{34}O_4$ C, 71.96 H, 9.78% Found C, 70.84 H, 9.93%

EXAMPLE 47

Preparation of 13,14-dihydro-3(ξ),16ξ)-dimethyl-prostaglandin-$A_2$ 286 g. of 13,14-dihydro-3(ξ),16(ξ)-dimethyl-prostaglandin-$E_2$ [prepared as described in Example 38] gave, after the same treatment as described in Example 45, 141 mg. (51.7%) of the title compound as an oil. IR absorption spectrum (liquid film): 3380, 2930, 2855, 2700 – 2300, 1740, 1710, 1585, 1245 – 1150 cm$^{-1}$; NMR spectrum (in $CDCl_3$, TMS as internal standard): δ: 0.75 – 1.05 (9H, multiplet)$_{ppm}$, 1.05 – 2.95 (20H, multiplet)$_{ppm}$, 3.50 – 3.82 (1H, multiplet)$_{ppm}$, 4.8 – 5.6 (4H, broad peak & multiplet)$_{ppm}$, 6.10 – 6.22 (1H, multiplet)$_{ppm}$, 7.55 – 7.70 (1H, multiplet)$_{ppm}$;

Elementary analysis: Calculated for $C_{22}H_{36}O_4$ C, 72.49 H, 9.96%. Found C, 72.74 H, 10.17%.

EXAMPLE 48

Preparation of 13,14-dihydro-15(ξ),16(R)-dimethyl-prostaglandin-$A_2$

Following the procedure of Example 43 but starting with 420 mg. of 13,14-dihydro-15(ξ),16(R)-dimethyl-prostaglandin-$E_2$ [prepared as described in Example 39], 219 mg. (54.3%) of the title compound was obtained as an oil. IR absorption spectrum (liquid film): 3400, 2930, 2855, 2700 – 2300, 1740, 1710, 1590, 1455, 1380, 1240 cm$^{-1}$; NMR spectrum (in $CDCl_3$, TMS as internal standard): δ: 0.75 – 1.05 (6H, multiplet)$_{ppm}$, 1.05 – 2.95 (24H, multiplet)$_{ppm}$, 4.3 – 4.8 (2H, broad peak)$_{ppm}$, 5.26 – 5.56 (2H, multiplet)$_{ppm}$, 6.08 – 6.20 (1H, multiplet)$_{ppm}$, 7.54 – 7.68 (1H, multiplet)$_{ppm}$;

Elementary analysis: Calculated for $C_{22}H_{36}O_4$ C, 72.49 H, 9.96%. Found C, 72.26 H, 9.75%.

EXAMPLE 49

Preparation of 2α-(6-carboxy-hex-cis-2-enyl)-3β-(3ξ-hydroxy-4(ξ)-phenyl-pentyl)-cyclopent-4-3n-1-one [or 16(ξ)-phenyl-ω-trinor-13,14-dihydroprostaglandin-$A_2$]

511 mg. of the product of Example 40 were dissolved in 60 ml. of a mixture of tetrahydrofuran and 1N hydrochloric acid (1:1) and the solution stirred at 60°C. for 3 hours. The reaction mixture was then poured into chilled water, extracted with ethyl acetate, washed well with water and dried. After concentration of the residue and column chromatography of the product using ethyl acetate – cyclohexane (1:4) as eluent, 277 mg. (56.8%) of the title compound was obtained as an oil. IR absorption spectrum (liquid film): 3370, 2920, 2700 – 2300, 1735, 1705, 1600, 1590, 1445, 1240 cm$^{-1}$; NMR spectrum (in $CDCl_3$, TMS as internal standard):δ: 1.1 – 3.0 (18H, multiplet)$_{ppm}$, 3.6 – 3.95 (1H, multiplet)$_{ppm}$, 4.8 – 5.3 (2H, broad peak)$_{ppm}$, 5.25 – 5.55 (2H, multiplet)$_{ppm}$, 6.10 – 6.28 (1H, multiplet)$_{ppm}$, 7.1 – 7.4 (5H, multiplet)$_{ppm}$, 7.43 – 7.55 (1H, multiplet)$_{ppm}$;

Elementary analysis: Calculated for $C_{23}H_{36}O_4$ C, 74.56 H, 8.16%. Found C, 74.77 H, 8.29%.

EXAMPLE 50

Preparation of
2α-(6carboxy-hex-cis-2-enyl)-3β-(3α-hydroxy-4(ξ)-cyclohexyl-pentyl)-cyclopent-4-en-1-one [or 16(ξ)-cyclohexyl-ω-trinor-13,14-dihydroprostaglandin-A$_2$]

665 mg. of the product of Example 41 was treated in the same way, the reaction mixture worked-up and the crude product purified, following the procedure of Example 43 to give 346 mg. (54.5%) of the title compound as an oil. IR absorption spectrum (liquid film): 3400, 2925, 2850, 2700 – 2300, 1740, 1710, 1590, 1450, 1380, 1245 cm$^{-1}$; NMR spectrum (in CDCl$_3$, TMS as internal standard): δ: 0.55 – 1.0 (3H, multiplet)$_{ppm}$, 1.05 – 2.95 (26H, multiplet)$_{ppm}$, 3.50 – 3.80 (1H, multiplet)$_{ppm}$, 4.1 – 4.8 (2H, broad peak)$_{ppm}$, 5.27 – 5.58 (2H, multiplet)$_{ppm}$, 6.10 – 6.22 (1H, multiplet)$_{ppm}$, 7.55 – 7.70 (1H, multiplet)$_{ppm}$;

Elementary analysis: Calculated as $C_{23}H_{36}O_4$ C, 73.36 H, 9.64%. Found C, 73.21 H, 9.50%.

EXAMPLE 51

Preparation of
2α-(6-carboxy-hex-cis-2-enyl)-3β-(3α-hydroxy-4(ξ)-cyclopentyl-butyl)-cyclopent-4-en-1-one [or 16(ξ)-cyclopentyl-ω-tetranor-13,14-dihydroprostaglandin-A$_2$]

485 mg. of the product of Example 42 gave 271 mg. (58.7%) of the title compound as an oil, following the procedure of Example 43. IR absorption spectrum (liquid film): 3400, 2930, 2855, 2700 – 2300, 1740, 1710, 1455, 1380, 1245 cm$^{-1}$; NMR spectrum (in CDCl$_3$, TMS as internal standard): δ: 1.05 – 2.95 (25H, multiplet)$_{ppm}$, 3.48 – 3.82 (1H, multiplet)$_{ppm}$, 4.8 – 5.3 (2H, broad peak)$_{ppm}$, 5.25 – 5.60 (2H, multiplet)$_{ppm}$, 6.10 – 6.22 (1H, multiplet)$_{ppm}$, 7.50–7.65 (1H, multiplet)$_{ppm}$;

Elementary analysis: Calculated for $C_{21}H_{32}O_4$ C, 72.38 H, 9.26%. Found C, 72.16 H, 9.13%.

EXAMPLE 52

Preparation of
2α-(6-carboxy-hex-cis-2-enyl)-3β-(3ξ-hydroxy-4(ξ)-cyclopentyl-pentyl)-cyclopentan-1α,4αdiol [or 16(ξ)-cyclopentyl-ω-trinor-13,14-dihydroprostaglandin-F$_{2α}$]

780 mg. of 2α-(6-carboxy-hex-cis-2-enyl)-3β-(3ξ-tetrahydropyranyloxy-4(ξ)-cyclopentyl-pentyl)-4α-tetrahydropyranyloxy-cyclopentan-1α-ol [prepared as described in Example 18] was dissolved in a mixture of 6 ml. of tetrahydrofuran, 5.4 ml. of water and 0.71 ml. of hydrochloric acid, and the solution stirred at room temperature for 2.5 hours. The reaction mixture was neutralized with aqueous sodium bicarbonate solution, extracted with ethyl acetate, washed with water, dried over magnesium sulphate, concentrated in vacuo and purified finally by column chromatography on silica gel using ethyl acetate and cyclohexane as eluent to give 318 mg. (59%) of the title compound as an oil. IR absorption spectrum (liquid film): 3350, 2950, 2860, 2700 – 2300, 1710, 1440, 1250, 1060 cm$^{-1}$; NMR spectrum (in CDCl$_3$, TMS as internal standard): δ0.75 ~ 0.96 (3H, doublet), 3.53 ~ 3.80 (1H, multiplet), 3.87 ~ 4.07 (1H, multiplet), 4.07 ~ 4.26 (1H, multiplet), 4.50 ~ 4.90 (4H, broad singlet), 5.30 ~ 5.60 (2H, multiplet).

EXAMPLE 53

Preparation of
2α-(6-carboxy-hex-cis-2-enyl)-3β-(3ξ-hydroxy-4(ξ)-cyclopentyl-pentyl)-4α-hydroxy-cyclopentanone [or 16(ξ)-cyclopentyl-ω-trinor-13,14-dihydroprostaglandin-E$_2$]

1.75 g. of the product of Example 18 was dissolved in 50 ml. of diethyl ether, and a chromic acid solution (chromic trioxide 2.6 g., manganese sulphate 12 g., conc. sulphuric acid 2.88 ml., and water 45 ml.) was added at 0°C., and the solution stirred at 0° – 5°C. for 3 hours. Diethyl ether was then added, the organic layer was separated and the aqueous layer extracted with diethyl ether. The combined ethereal layers were washed with water, dried and concentrated in vacuo to produce crude 2α-(6-carboxy-hex-cis-2-enyl)-3β-(3ξ-tetrahydropyranyloxy-4(ξ)-cyclopentyl-pentyl)-4α-tetrahydropyranyloxy-cyclopentanone. The crude product was dissolved in 23 ml. of a mixture of acetic acid, water and tetrahydrofuran (20:10:3) and the solution stirred at 38° – 40°C. for 3.5 hours. The reaction mixture was then poured into 150 ml. of water and extracted with ethyl acetate. The organic layer was washed, dried and concentrated in vacuo. The residue was purified by column chromatography on silica gel using ethyl acetate-cyclohexane as eluent to give 568 mg. (47%) of the title compound as an oil. IR absorption spectrum (liquid film): 3400, 2940, 2860, ~2300, 1730, 1705, 1460, 1405, 1380, 1250, 1180, 1080 cm$^{-1}$; NMR spectrum (in CDCl$_3$, TMS as internal standard): δ: 0.70 ~ 0.96 (3H, doublet), 2.55 ~ 2.88 (1H, quartet), 3.50 ~3.84 (1H, multiplet), 4.00 ~ 4.37 (1H, multiplet), 4.37 ~ 4.80 (3H, broad singlet), 5.34 ~ 5.55 (2H, multiplet).

EXAMPLE 54

Preparation of
2α-(6-carboxy-hex-cis-2-enyl)-3β-(3ξ-hydroxy-4(ξ)-cyclopentyl-pentyl)-cyclopent-4-en-1-one [or 16(ξ)-cyclopentyl-ω-trinor-13,14-dihydroprostaglandin-A$_2$]

340 mg. of 2α-(6-carboxy-hex-cis-2-enyl)-3β-(3ξ-hydroxy-4(ξ)-cyclopentyl-pentyl)-4α-hydroxy-cyclopentanone [prepared as described in Example 53] were dissolved in 25 ml. of a mixture of tetrahydrofuran and 1N hydrochloric acid (1:1) and the solution stirred at 60°C. for 3 hours. The reaction mixture was then poured into ice-water, extracted with ethyl acetate, and the organic layer was washed with water and saturated sodium chloride solution, dried over sodium sulphate and concentrated in vacuo. The residue was subjected to column chromatography on silica gel using cyclohexaneethyl acetate as eluent which gave 194 mg. (60%) of the title compound as an oil. IR absorption spectrum (liquid film): 3420, 2950, 2860, ~2350, 1740, 1710, 1590, 1440, 1400, 1380, 1360, 1080 cm$^{-1}$; NMR spectrum (in CDCl$_3$, TMS as internal standard): δ: 0.75 ~ 0.95 (3H, doublet), 3.48 ~ 3.83 (1H, multiplet), 4.60 ~ 5.05 (2H, broad singlet), 5.30 ~ 5.55 (2H, multiplet), 6.10 ~ 6.22 (1H, quartet), 7.55 ~ 7.73 (1H, multiplet).

EXAMPLE 55

Preparation of methyl ester of 13,14-dihydro-16(R)-methylprostaglandin-$E_2$

A newly prepared ethereal solution of diazomethane was added to 450 mg. of 13,14-dihydro-16(R)-methyl-prostaglandin-$E_2$ [cf. Example 33] until a light yellow colour did not vanish. After stirring at 0°C. for 2 to 3 minutes, the excess of diazomethane was decomposed with a dilute ethereal solution of acetic acid, and the reaction mixture was concentrated under reduced pressure. The residue was purified by column chromatography on 20 g. of silica gel using cyclohexaneethyl acetate (6:4) as eluent to give 349 mg. of pure methyl ester of 13,14-dihydro-16(R)-methyl-prostaglandin-$E_2$ as a colourless oil, (yield 75%). IR absorption spectrum (liquid film): 3400, 2950 ~ 2850, 1740, 1730, 1460 ~ 1440, 1380, 1320, 1250, 1200, 1185, 1080 $cm^{-1}$; NMR spectrum (in $CDCl_3$, TMS as internal standard): δ: 0.75 ~ 1.03 (6H, multiplet), 2.55 ~ 2.84 (1H, quartet), 3.40 ~ 3.65 (1H, multiplet), 3.67 (3H, singlet), 4.05 ~ 4.30 (1H, multiplet), 5.30 ~ 5.54 (2H, multiplet).

EXAMPLE 56

Preparation of isobutyl ester of 13,14-dihydro-16(R)-methylprostaglandin-$E_2$

From 370 mg. of 13,14-dihydro-16(R)-methylprostaglandin-$E_2$ and a freshly prepared ethereal solution of diazoisobutane, there was obtained 291 mg (68%) of the corresponding isobutyl ester as an oil, following the same procedure as in Example 55; IR absorption spectrum (liquid film): 3420, 2960 ~ 2850, 1740, 1480, 1385, 1250, 1160, 1080 $cm^-$; NMR spectrum (in $CDCl_3$, TMS as internal standard): δ: 0.78 ~ 1.04 (12H, multiplet), 2.56 ~ 2.86 (1H, quartet), 3.40 ~ 3.65 (1H, multiplet), 3.82 ~ 3.92 (2H, doublet), 4.05 ~ 4.30 (1H, multiplet), 5.30 ~ 5.60 (2H, multiplet).

EXAMPLE 57

Preparation of n-decyl ester of 13,14-dihydro-16(R)-methyl-prostaglandin-$E_2$

From 1.03 g. of 13,14-dihydro-16(R)-methyl-prostaglandin-$E_2$ and a freshly prepared ethereal solution of diazo-n-decane, there was obtained in a yield of 70% the corresponding n-decyl ester in the form of an oil, following the same procedure as in Example 55. IR absorption spectrum (liquid film): 3400, 2940 ~ 2840, 1730, 1460, 1380, 1310, 1240, 1160, 1080 $cm^{-1}$; NMR spectrum (in $CDCl_3$, TMS as internal standard): δ: 0.75 ~ 1.02 (9H, multiplet), 2.55 ~ 2.84 (1H, quartet), 3.40 ~ 3.60 (1H, multiplet), 3.96 ~ 4.23 (2H, triplet), 5.30 ~ 5.50 (2H, multiplet).

The present invention includes within its scope pharmaceutical compositions which comprise at least one new therapeutically active prostaglandin compound according to the present invention, together with a pharmaceutical carrier or coating. In clinical practice such novel compounds will normally be administered orally, rectally, vaginally or parenterally.

Solid compositions for oral administration include compressed tablets, pills dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.05 and 5 mg/kg body weight by oral administration in the prevention or treatment of hypertension, between 0.5 and 100 μg/kg body weight by oral administration in the prevention and treatment of gastric ulceration, between 0.1 and 50 μg/kg body weight by aerosol administration in the treatment of asthma, between 20 and 500 μg/kg body weight by vaginal administration in the control of oestrus in female mammals, between 20 μg and 1 mg/kg body weight by extraamniotic administration in the prevention of pregnancy in female mammals, between 10 and 500 μg/kg body weight by extraamniotic administration in the induction of labor in pregnant female mammals.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 1 to 100 μg., and more particularly 10 to 50 μg, of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants having vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 1 to 100 μg., and more particularly 10 to 50 μg., of active ingredient per ml. of solution or suspension. It is important that the pH of solutions and suspensions used, according to the present invention, to generate aerosols should be kept within the range 3 to 8 and preferable that they should be stored at or below 4°C., to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 58

16(R)-methyl-13,14-dihydro-$PGE_2$ (500 $\mu$g.) was dissolved in ethanol (1 ml.) and the solution obtained was added to an aqueous solution (12 ml.) containing sodium carbonate (50 mg.). Aqueous sodium chloride solution (0.9% w/v, 2 ml.) was then added to give a final volume of 15 ml. The solution was then sterilized by passage through a bacteria-retaining filter and placed in 1.5 ml. portions in 5 ml. ampoules, to give 50 $\mu$g. of 16(R)-methyl-13,14-dihydro-$PGE_2$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 59

16(R)-methyl-13,14-dihydro-$PGE_2$ (20 mg.) was dissolved in ethanol (10 ml.), mixed with mannitol (18.5 g.), sieved through a 30-mesh sieve, dried at 30°C. for 90 minutes and again sieved through a 30-mesh sieve. Aerosil (microfine silica) (200 μg) was added and the powder obtained was machine-filled into one hundred No. 2 hard gelatin capsules to give capsules each containing 200 μg. of 16(R)-methyl-13,14-dihydro-PGE$_2$ which after swallowing is released into the stomach.

We claim:
1. 15($\xi$)-Methyl-13,14-dihydro-PGF$_{2\alpha}$.
2. 15($\xi$),16(R)-Dimethyl-13,14-dihydro-PGF$_{2\alpha}$.
3. 16($\xi$)-Phenyl-ω-trinor-13,14-dihydro-PGF$_{2\alpha}$.
4. 16($\xi$)-Cyclohexyl-ω-trinor-13,14-dihydro-PGF$_{2\alpha}$.
5. 16($\xi$)-Cyclopentyl-ω-tetranor-13,14-dihydro-PGF$_{2\alpha}$.
6. 16($\xi$)-Cyclopentyl-ω-trinor-13,14-dihydro-PGF$_{2\alpha}$.

* * * * *